(12) United States Patent
Choi et al.

(10) Patent No.: US 11,707,486 B2
(45) Date of Patent: *Jul. 25, 2023

(54) NATURAL KILLER CELL EXPRESSING ANTI-COTININE CHIMERIC ANTIGEN RECEPTOR

(71) Applicants: KOREA RESEARCH INSTITUTE OF BIOSCIENCE AND BIOTECHNOLOGY, Daejeon (KR); SEOUL NATIONAL UNIVERSITY R&DB FOUNDATION, Seoul (KR)

(72) Inventors: In Pyo Choi, Daejeon (KR); Tae-Don Kim, Daejeon (KR); Su Ui Lee, Daejeon (KR); Sooyun Lee, Daejeon (KR); Junho Chung, Seongnam-si (KR); Ki-Hyun Kim, Seoul (KR); Hyori Kim, Seoul (KR)

(73) Assignees: KOREA RESEARCH INSTITUTE OF BIOSCIENCE AND BIOTECHNOLOGY, Daejeon (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 655 days.

This patent is subject to a terminal disclaimer.

(21) Appl. No.: 16/503,984

(22) Filed: Jul. 5, 2019

(65) Prior Publication Data

US 2019/0365815 A1    Dec. 5, 2019

Related U.S. Application Data

(63) Continuation-in-part of application No. PCT/KR2018/000310, filed on Jan. 5, 2018.

(30) Foreign Application Priority Data

Jan. 5, 2017 (KR) .................. 10-2017-0001951
Jan. 5, 2017 (KR) .................. 10-2017-0001976

(51) Int. Cl.

| | |
|---|---|
| *A61K 35/17* | (2015.01) |
| *A61P 35/00* | (2006.01) |
| *C07K 14/705* | (2006.01) |
| *C07K 14/725* | (2006.01) |
| *A61K 38/00* | (2006.01) |
| *A61K 39/00* | (2006.01) |
| *C07K 16/16* | (2006.01) |
| *C07K 16/28* | (2006.01) |

(52) U.S. Cl.
CPC .............. *A61K 35/17* (2013.01); *A61P 35/00* (2018.01); *C07K 14/7051* (2013.01); *C07K 14/70503* (2013.01); *C07K 14/70517* (2013.01); *C07K 14/70521* (2013.01); *C07K 16/16* (2013.01); *C07K 16/2863* (2013.01); *A61K 38/00* (2013.01); *A61K 2039/505* (2013.01); *C07K 2317/30* (2013.01); *C07K 2317/622* (2013.01); *C07K 2317/732* (2013.01); *C07K 2317/734* (2013.01); *C07K 2317/76* (2013.01); *C07K 2319/02* (2013.01); *C07K 2319/03* (2013.01); *C07K 2319/30* (2013.01); *C07K 2319/33* (2013.01)

(58) Field of Classification Search
CPC ... A61K 35/17; A61K 2039/505; A61P 35/00; C07K 14/7051; C07K 2317/622; C07K 2319/02; C07K 2319/03; C07K 16/44
See application file for complete search history.

(56) References Cited

U.S. PATENT DOCUMENTS

| | | |
|---|---|---|
| 2004/0043401 A1 | 3/2004 | Sadelain et al. |
| 2008/0226650 A1* | 9/2008 | Park .................. A61P 25/30 424/141.1 |
| 2011/0189206 A1* | 8/2011 | Barbas, III .......... G01N 33/6845 424/178.1 |
| 2013/0287752 A1 | 10/2013 | Davila et al. |
| 2014/0056926 A1 | 2/2014 | Chung et al. |
| 2015/0051266 A1 | 2/2015 | Kochenderfer et al. |
| 2015/0238631 A1 | 8/2015 | Kim et al. |
| 2016/0075784 A1 | 3/2016 | Yu et al. |
| 2016/0130357 A1 | 5/2016 | Mukherjee et al. |
| 2016/0361360 A1* | 12/2016 | Chang .................. A61P 1/16 |

(Continued)

FOREIGN PATENT DOCUMENTS

| | | |
|---|---|---|
| CN | 103483453 A | 1/2014 |
| EP | 2 700 653 A2 | 2/2014 |

(Continued)

OTHER PUBLICATIONS

Park et al.Cotinine-conjugated aptamer/anti-cotinine antibody complexes as a novel affinity unit for use in biological assays. Experimental and Molecular Medicine, vol. 44, No. 9, 554-561, Sep. 2012. (Year: 2011).*

(Continued)

*Primary Examiner* — Amy E Juedes
*Assistant Examiner* — Brian Hartnett
(74) *Attorney, Agent, or Firm* — Sughrue Mion, PLLC

(57) ABSTRACT

Disclosed are a natural killer (NK) cell expressing an anti-cotinine chimeric antigen receptor (CAR) specifically binding to cotinine, and a cell therapeutic agent containing the NK cell. The CAR-expressing NK cell which specifically binds cotinine, can effectively move to tumor tissue, regardless of the kind of cancer, depending on the binding substance bound to cotinine. Therefore, the natural killer cell can be usefully employed as a gene therapy exhibiting a highly efficient anticancer effect.

15 Claims, 26 Drawing Sheets

Specification includes a Sequence Listing.

(56) References Cited

U.S. PATENT DOCUMENTS

| | | | |
|---|---|---|---|
| 2018/0066034 | A1 | 3/2018 | Ma et al. |
| 2018/0256744 | A1 | 9/2018 | Choi et al. |

FOREIGN PATENT DOCUMENTS

| | | | | |
|---|---|---|---|---|
| JP | 2011509084 A | 3/2011 | | |
| KR | 10-2014-0027219 A | 3/2014 | | |
| WO | 2009/088805 A2 | 7/2009 | | |
| WO | 2012/141554 A2 | 10/2012 | | |
| WO | 2013/044225 A1 | 3/2013 | | |
| WO | 2014/100615 A1 | 6/2014 | | |
| WO | 2015/080981 A1 | 6/2015 | | |
| WO | 2016/030414 A1 | 3/2016 | | |
| WO | 2016/123333 A1 | 8/2016 | | |
| WO | 2016/126608 A1 | 8/2016 | | |
| WO | 2016/168773 A2 | 10/2016 | | |
| WO | 2016/210293 A1 | 12/2016 | | |
| WO | 2017/030370 A1 | 2/2017 | | |
| WO | WO-2017030370 A1 * | 2/2017 | ............ | A61K 35/17 |

OTHER PUBLICATIONS

Lloyd et al. Modelling the human immune response: performance of a 10^11 human antibody repertoire against a broad panel of therapeutically relevant antigens. Protein Engineering, Design & Selection vol. 22 No. 3 pp. 159-168, 2009. (Year: 2009).*

WO-2017030370-A1. Google Translate Document. (Year: 2017).*

Cartellieri, et al., "Switching CAR T cells on and off: a novel modular platform for retargeting of T cells to AML blasts", Blood Cancer Journal, 2016, pp. 1-8, vol. 6, No. 8 (8 pages total).

European Patent Office; Communication dated Jan. 3, 2019 in application No. 16837312.4.

Herve Bouchard et al., "Antibody-drug conjugates—A new wave of cancer drugs", Bioorganic & Medicinal Chemistry Letters, Oct. 13, 2014, vol. 24, No. 23, pp. 5357-5363 (6 pages total).

International Search Report for PCT/KR2016/009047 dated Nov. 11, 2016.

Urbanska, et al., "A Universal Strategy for Adoptive Immunotherapy of Cancer through Use of a Novel T-cell Antigen Receptor", Cancer Research, Feb. 7, 2012, pp. 1844-1852, vol. 72, No. 7 (10 pages total).

Rudikoff et al., "Single amino acid substitution altering antigen-binding specificity", Proc. Natl. Acad. Sci. USA, 1982, vol. 79, pp. 1979-1983 (5 pages total).

Mariuzza et al., "The Structural Basis of Antigen-Antibody Recognition", Ann. Rev. Biophys. Chem., 1987, vol. 16, pp. 139-159 (21 pages total).

Gussow et al., "Humanization of Monoclonal Antibodies", Methods in Enzymology, 1991, vol. 203, pp. 99-121 (23 pages total).

Giusti et al., "Somatic diversification of S107 from an antiphosphocholine to an anti-DNA autoantibody is due to a single base change in its heavy chain variable region", Proc. Natl. Acad. Sci. USA, 1987, vol. 84, pp. 2926-2930 (5 pages total).

Winkler et al., "Changing the Antigen Binding Specificity by Single Point Mutations of an Anti-p24 (HIV-1) Antibody", Journal of Immunology, 2000, vol. 165, pp. 4505-4514 (10 pages total).

Chien et al., "Significant structural and functional change of an antigen-binding site by a distant amino acid substitution: Proposal of a structural mechanism", Proc. Natl. Acad. Sci. USA, 1989, vol. 86, pp. 5532-5536 (5 pages total).

Caldas et al., "Humanization of the anti-DC18 antibody 6.7: an unexpected effect of a framework residue in binding to antigen", Molecular Immunology, 2003, vol. 39, pp. 941-952 (12 pages total).

Vajdos et al., "Comprehensive Functional Maps of the Antigen-binding Site of an Anti-ErbB2 Antibody Obtained with Shotgun Scanning Mutagenesis", J. Mol. Biol., 2002, vol. 320, pp. 415-428 (14 pages total).

De Pascalis et al., "Grafting of "Abbreviated" Complementarity-Determining Regions Containing Specificity-Determining Residues Essential for Ligand Contact to Engineer a Less Immunogenic Humanized Monoclonal Antibody", The Journal of Immunology, 2002, vol. 169, pp. 3076-3084 (9 pages total).

Wu et al., "Humanization of a Murine Monoclonal Antibody by Simultaneous Optimization of Framework and CDR Residues", J. Mol. Biol., 1999, vol. 294, pp. 151-162 (12 pages total).

Casset et al., "A peptide mimetic of an anti-CD4 monoclonal antibody by rational design", Biochemical and Biophysical Research Communications, 2003, vol. 307, pp. 198-205 (8 pages total).

MacCallum et al., "Antibody-antigen Interactions: Contact Analysis and Binding Site Topography", J. Mol. Biol., 1996, vol. 262, pp. 732-745 (14 pages total).

Holm et al., "Functional mapping and single chain construction of the anti-cytokeratin 8 monoclonal antibody TS1", Molecular Immunology, 2007, vol. 44, pp. 1075-1084 (10 pages total).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cell Biology, 1990, Vo. 111, pp. 2129-2138 (10 pages total).

Bridgeman et al., "The Optimal Antigen Response of Chimeric Antigen Receptors Harboring the CD3 ζ Transmembrane Domain is Dependent upon Incorporation of the Receptor into the Endogenous TCR/CD3 Complex", The Journal of Immunology, 2010, vol. 184, pp. 6938-6949 (13 pages total).

Hudecek et al., "Receptor Affinity and Extracellular Domain Modifications Affect Tumor Recognition by ROR1-Specific Chimeric Antigen Receptor T Cells", Clinical Cancer Research, 2013, vol. 19, No. 12, pp. 3153-3164 (13 pages total).

Park et al., "Cotinine-conjugated aptamer/anti-cotinine antibody complexes as a novel affinity unit for use in biological assays", Experimental and Molecular Medicine, 2012, vol. 44, No. 9, pp. 554-561 (8 pages total).

Park et al., "A sensitive enzyme immunoassay for measuring cotinine in passive smokers", Clinica Chimica Acta, 2010, vol. 411, pp. 1238-1242 (5 pages total).

Arndt et al., "Redirection of Immune Effector Cells by Bispecific Antibody Systems for the Treatment of Acute Myeloid Leukemia", Blood, 2011, vol. 118, No. 21: 1528 (7 pages total).

Arndt et al., "Costimulation improves the killing capability of T cells redirected to tumor cells expressing low levels of CD33: description of a novel modular targeting system", Leukemia, 2014, vol. 28, pp. 59-69 (11 pages total).

Tamada et al., "Redirecting Gene-Modified T Cells toward Various Cancer Types Tagged Antibodies", Clinical Cancer Research, 2012, vol. 18, No. 23, pp. 6436-6445 (11 pages total).

Kim et al., "Redirection of Genetically Engineered CAR-T Cells Using Bifunctional Small Molecules", Journal of the American Chemical Society, 2015, vol. 137, pp. 2832-2835 (4 pages total).

Ma et al., "Versatile strategy for controlling the specificity and activity of engineered T cells", PNAS, 2016, E-450-E458 (9 pages total).

Rodgers et al., "Switch-mediated activation and retargeting of CAR-T cells for B-cell malignancies", PNAS, 2016, E459-E468 (10 pages total).

Eshhar et al., "Specific activation and targeting of cytotoxic lymphocytes through chimeric single chains consisting of antibody-binding domains and the γ or ζ subunits of the immunoglobulin and T-cell receptors", Proc. Natl. Acad. Sci. USA, 1993, vol. 90, pp. 720-724 (5 pages total).

Sadelain et al., "The Basic Principles of Chimeric Antigen Receptor Design", Cancer Discov., 2013, vol. 3, No. 4, pp. 388-398 (11 pages total).

Gross et al., "Expression of immunoglobulin-T-cell receptor chimeric molecules as functional receptors with antibody-type specificity", Proc. Natl. Acad. Sci. USA, 1989, vol. 86, pp. 10024-10028 (5 pages total).

Kenderian et al., "Chimeric Antigen Receptor T-cell Therapy to Target Hematologic Malignancies", Cancer Res., 2014, vol. 74, No. 22, pp. 6383-6389 (8 pages total).

Zhao et al., "A Herceptin-Based Chimeric Antigen Receptor with Modified Signaling Domains Leads to Enhanced Survival of Transduced

(56) References Cited

OTHER PUBLICATIONS

T Lymphocytes and Antitumor Activity", The Journal of Immunology, 2009, vol. 183, pp. 5563-5574 (13 pages total).

Albanza et al., "Function of Novel Anti-CD19 Chimeric Antigen Receptors with Human Variable Regions Is Affected by Hinge and Transmembrane Domains", Molecular Therapy, 2017, vol. 25, No. 11, pp. 2452-2465 (14 pages total).

Fujiwara et al., "Hinge and Transmembrane Domains of Chimeric Antigen Receptor Regulate Receptor Expression and Signaling Threshold", Cells, 2020, vol. 9, No. 1182, pp. 1-17 (17 pages total).

Yu-Hsiang Chang et al., "A Chimeric Receptor with NKG2D Specificity Enhances Natural Killer Cell Activation and Killing of Tumor Cells", Cancer Research, vol. 73, No. 6, pp. 1777-1786, Mar. 2013 (11 pages total).

Connie P. M. Duong et al., "Engineering T Cell Function Using Chimeric Antigen Receptors Identified Using a DNA Library Approach", PLOS ONE, vol. 8, issue 5, e63037, pp. 1-10, May 2013 (10 pages total).

K. Heo et al., "An aptamer-antibody complex (oligobody) as a novel delivery platform for targeted cancer therapies", Journal of Controlled Release, 2016, vol. 229, pp. 1-9.

H. Kim et al., "In vitro and in vivo application of anti-cotinine antibody and cotinine-conjugated compounds", BMB Reports, 2014, vol. 47, No. 3, pp. 130-134.

H. Park et al., "Anti-cotinine CAR-modified T cells provides a novel switchable CAR platform using cotinine-conjugated adaptor molecules", The Journal of Immunology, May 1, 2017, vol. 198 (1 Supplement) 73.22, 1 page (abstract only).

International Search Report for PCT/KR2018/000310 dated Apr. 24, 2018 [PCT/ISA/210].

Written Opinion for PCT/KR2018/000310 dated Apr. 24, 2018 [PCT/ISA/237].

Magistrelli et al., "Identification of Three Alternatively Spliced Variants of Human CD28 mRNA", Biochemical and Biophysical Research Communications, 1999, vol. 259, pp. 34-37 (4 pages total).

* cited by examiner

[Fig. 1]
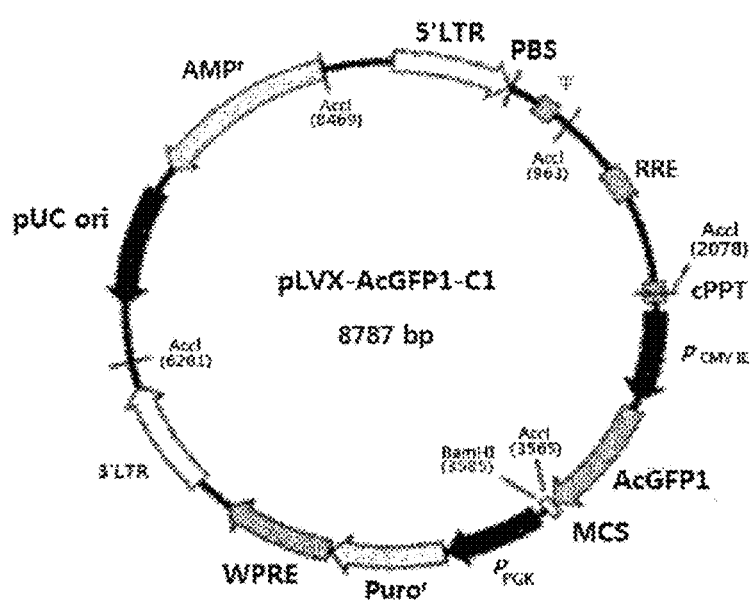

[Fig. 2]
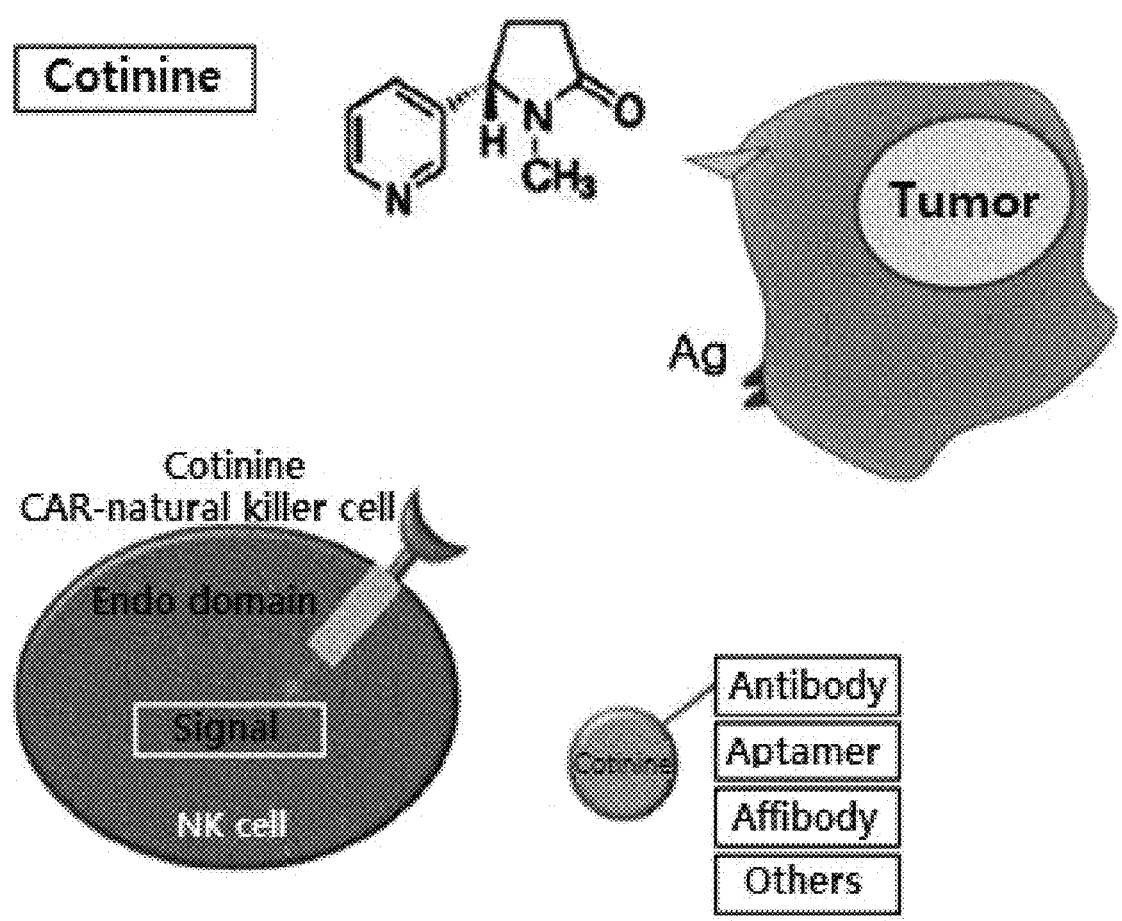

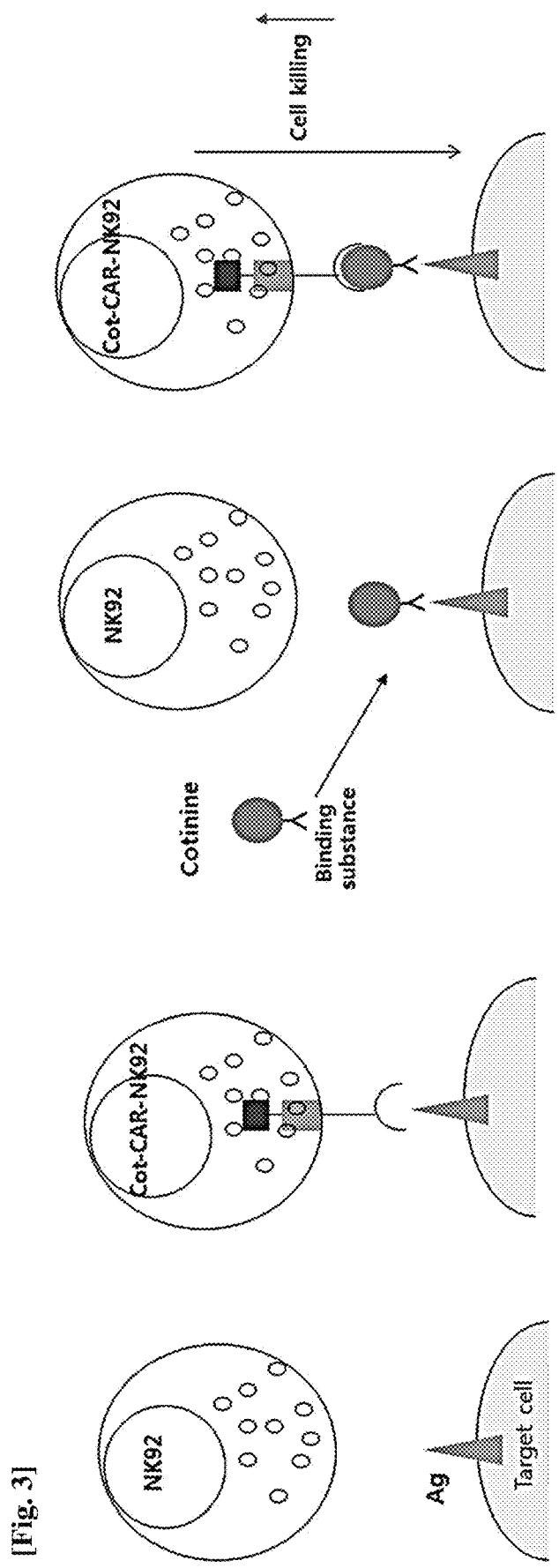

[Fig. 4]

```
                                                            CMV IE Promoter
2341   AAACTGCCCA  CTTGGCAGTA  CATCAAGTGT  ATCATATGCC  AAGTACGCCC  CCTATTGACG
       TTTGACGGGT  GAACCGTCAT  GTAGTTCACA  TAGTATACGG  TTCATGCGGG  GGATAACTGC
                                                            CMV IE Promoter
2401   TCAATGACGG  TAAATGGCCC  GCCTGGCATT  ATGCCCAGTA  CATGACCTTA  TGGGACTTTC
       AGTTACTGCC  ATTTACCGGG  CGGACCGTAA  TACGGGTCAT  GTACTGGAAT  ACCCTGAAAG
                                                            CMV IE Promoter
2461   CTACTTGGCA  GTACATCTAC  GTATTAGTCA  TCGCTATTAC  CATGGTGATG  CGGTTTTGGC
       GATGAACCGT  CATGTAGATG  CATAATCAGT  AGCGATAATG  GTACCACTAC  GCCAAAACCG
                                                            CMV IE Promoter
2521   AGTACATCAA  TGGGCGTGGA  TAGCGGTTTG  ACTCACGGGG  ATTTCCAAGT  CTCCACCCCA
       TCATGTAGTT  ACCCGCACCT  ATCGCCAAAC  TGAGTGCCCC  TAAAGGTTCA  GAGGTGGGGT
                                                            CMV IE Promoter
2581   TTTGACGTCA  TGGGAGTTTG  TTTTGGCACC  AAAATCAACG  GGACTTTCCA  AAATGTCGTA
       AACTGCAGTT  ACCCTCAAAC  AAAACCGTGG  TTTTAGTTGC  CCTGAAAGGT  TTTACAGCAT
                                                            CMV IE Promoter
2641   ACAACTCCGC  CCCATTGACG  CAAATGGGCG  GTAGGCGTGT  ACGGTGGGAG  GTCTATATAA
       TGTTGAGGCG  GGGTAACTGC  GTTTACCCGC  CATCCGCACA  TGCCACCCTC  CAGATATATT
                                                            CMV IE Promoter
2701   GCAGAGCTCG  TTTAGTGAAC  CGTCAGATCG  CCTGGAGACG  CCATCCACGC  TGTTTTTGAC
       CGTCTCGAGC  AAATCACTTG  GCAGTCTAGC  GGACCTCTGC  GGTAGGTGCG  ACAAAACTGG
                                                            AcGFP1
2761   TCCATAGAAG  ACACCGACTC  TACTAGAGGA  TCTACCCGTC  ▭▭▭▭▭▭▭▭▭  ▭▭▭▭▭▭▭▭▭▭
       AGGTATCTTC  TGTGGCTGAG  ATGATCTCCT  AGATGGGCAG  ▭▭▭▭▭▭▭▭▭  ▭▭▭▭▭▭▭▭▭▭
```

Kozak Sequence deleted

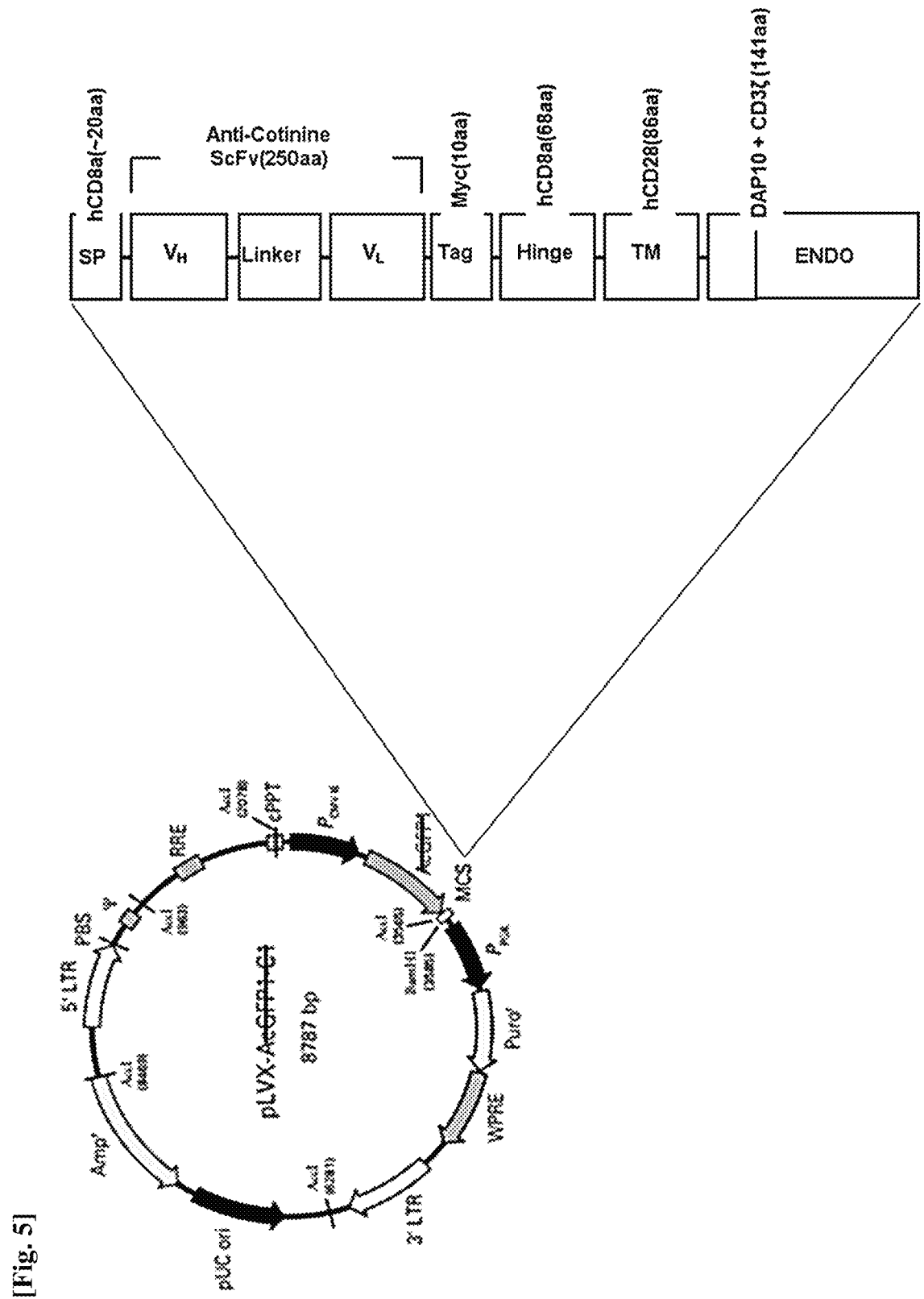
[Fig. 5]

[Fig. 6]
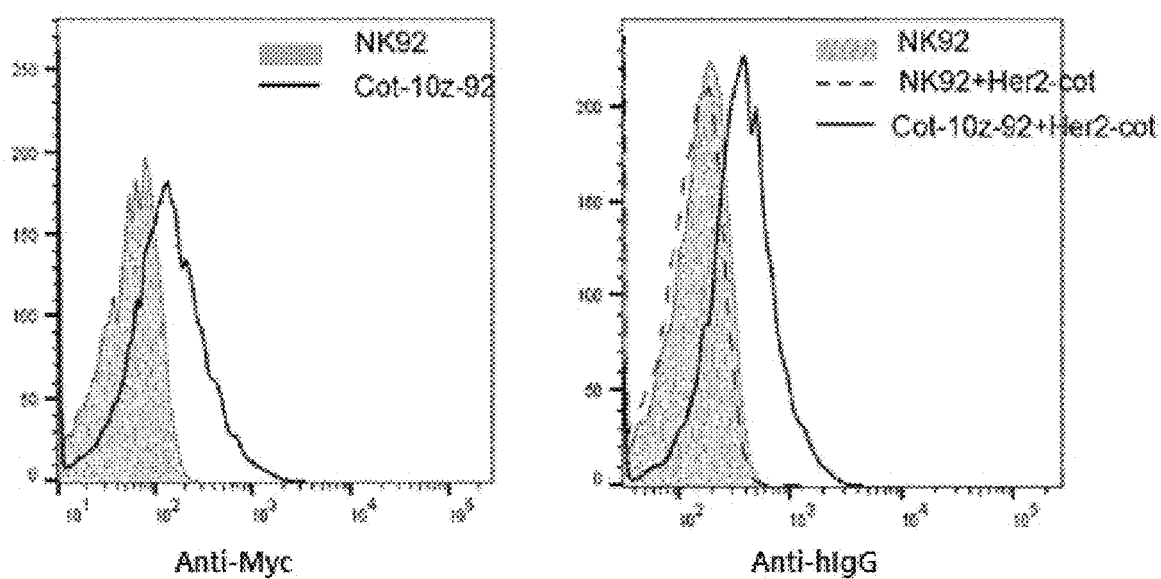

[Fig. 7]
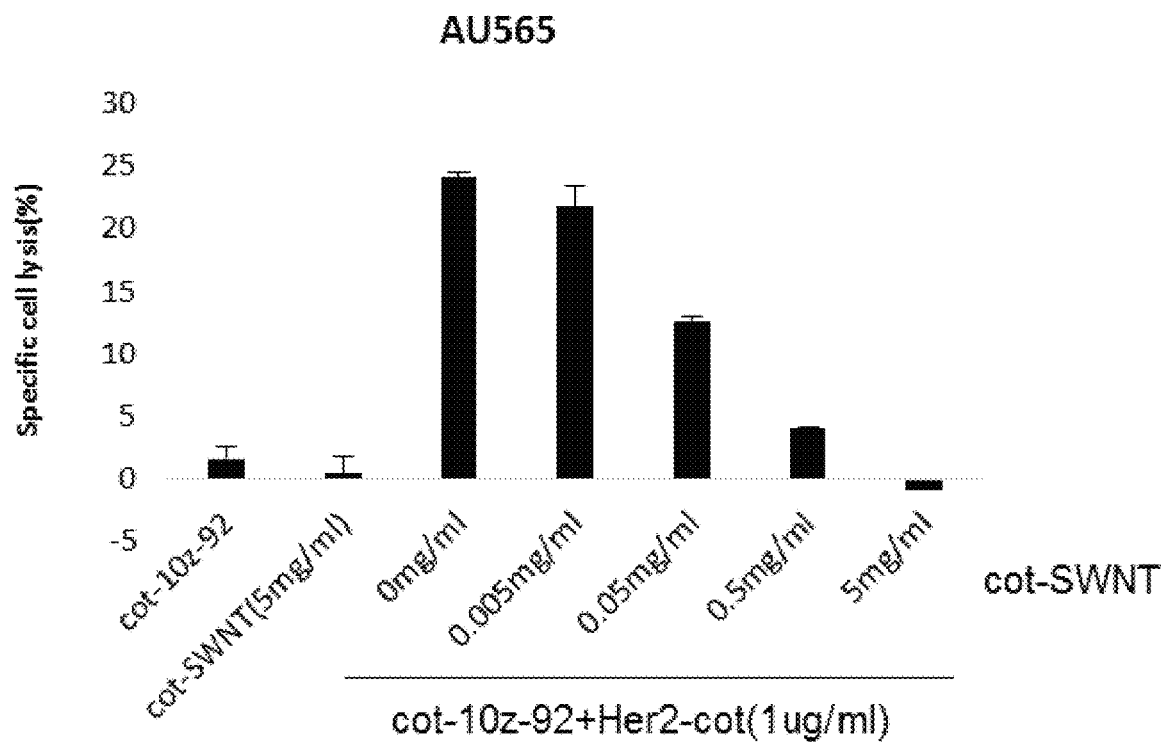

[Fig. 8]
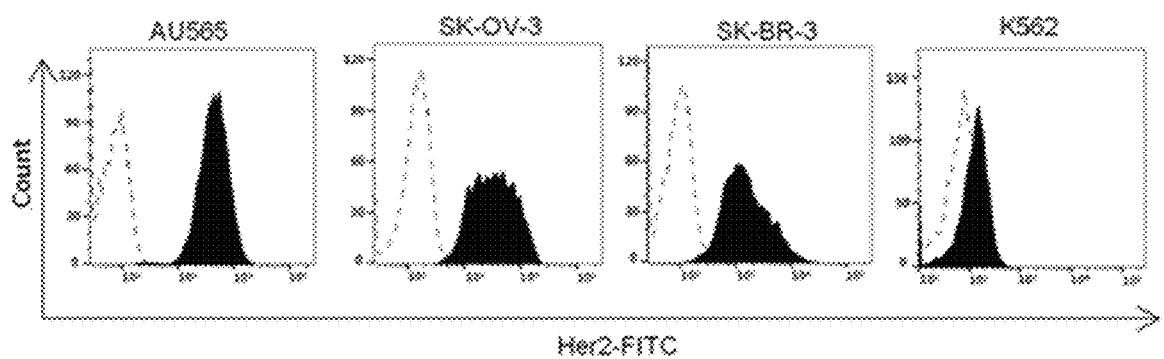

[Fig. 9]
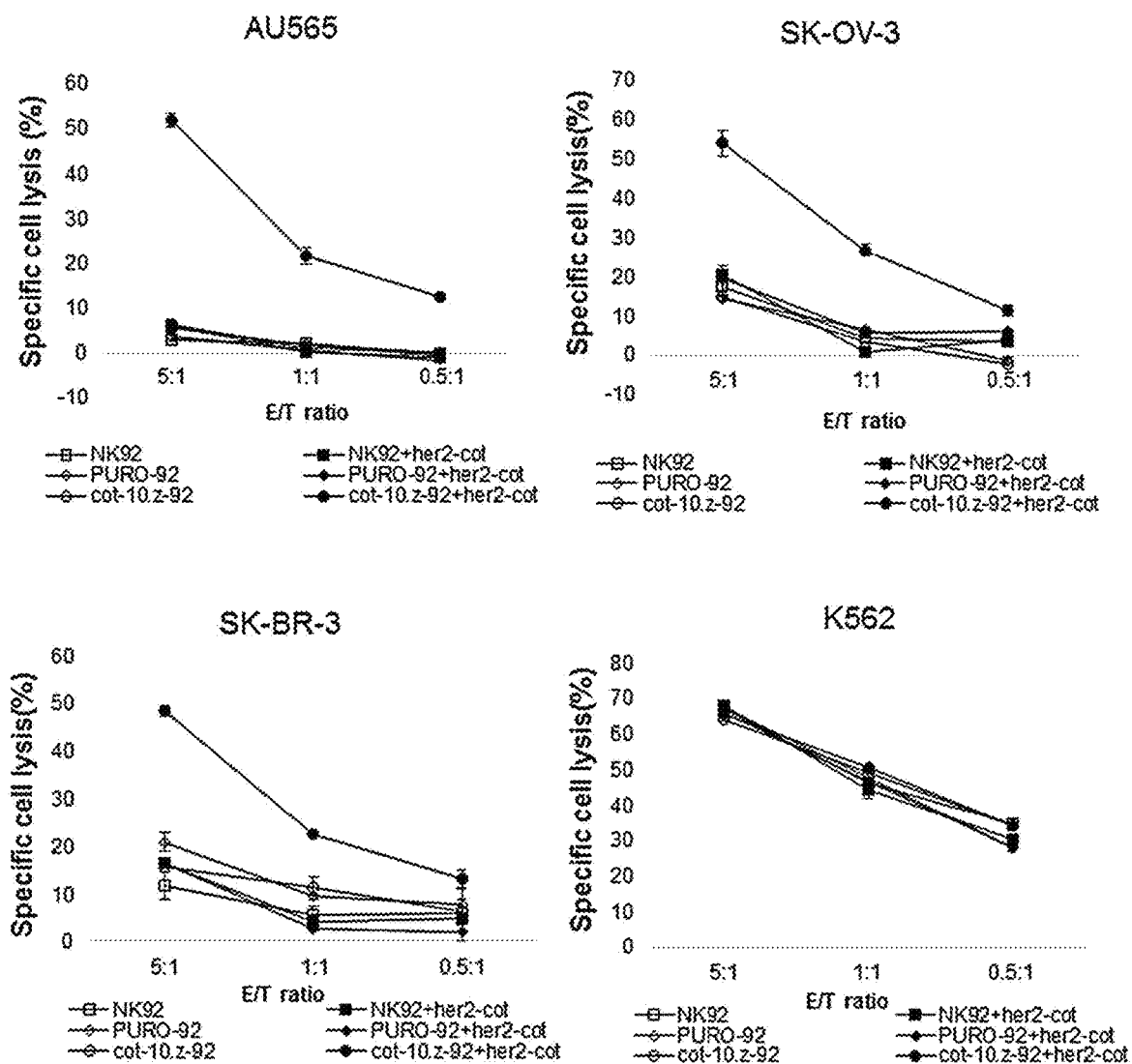

[Fig. 10]
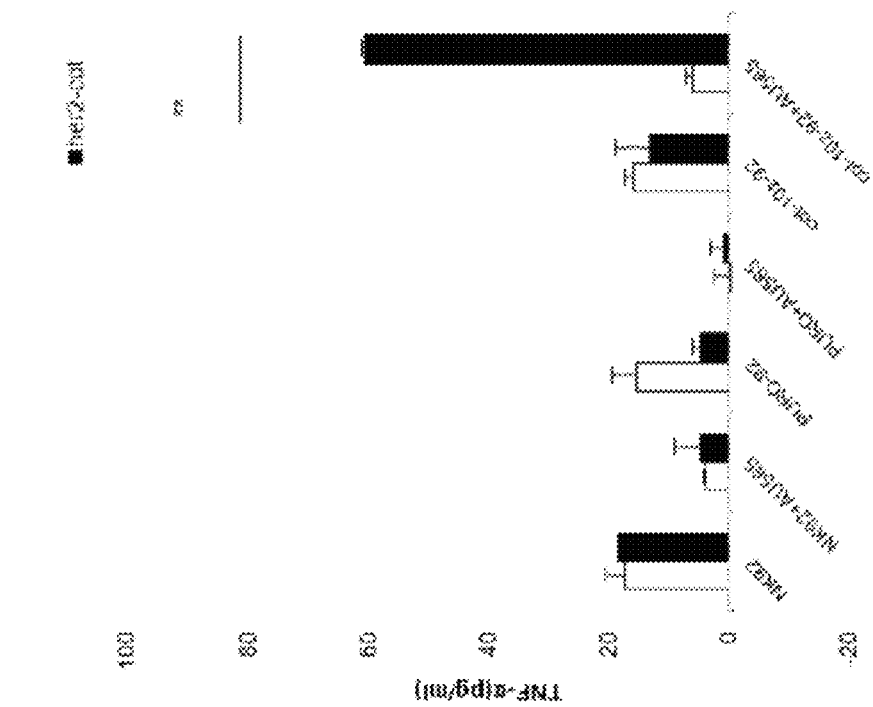
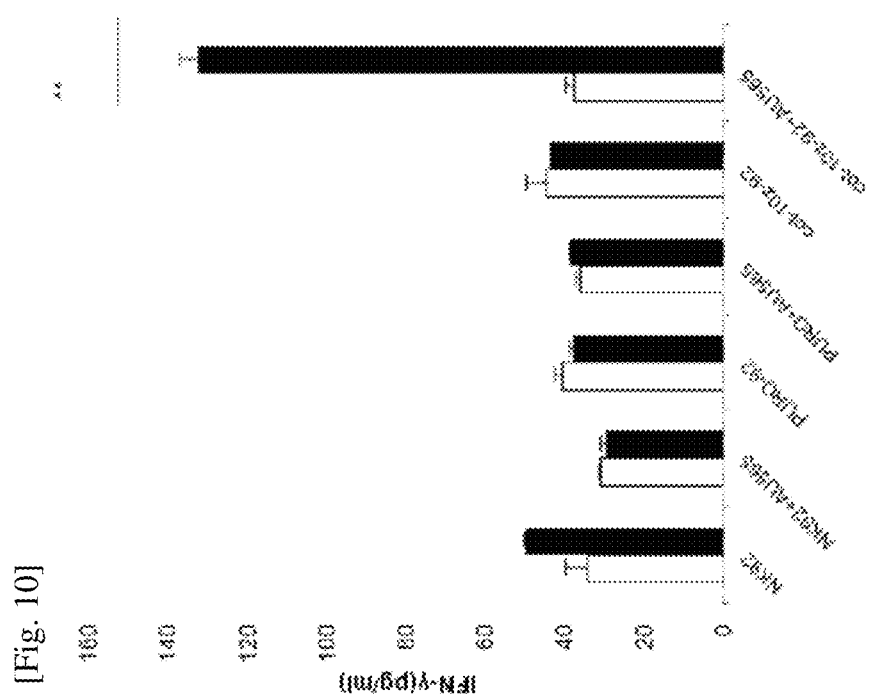

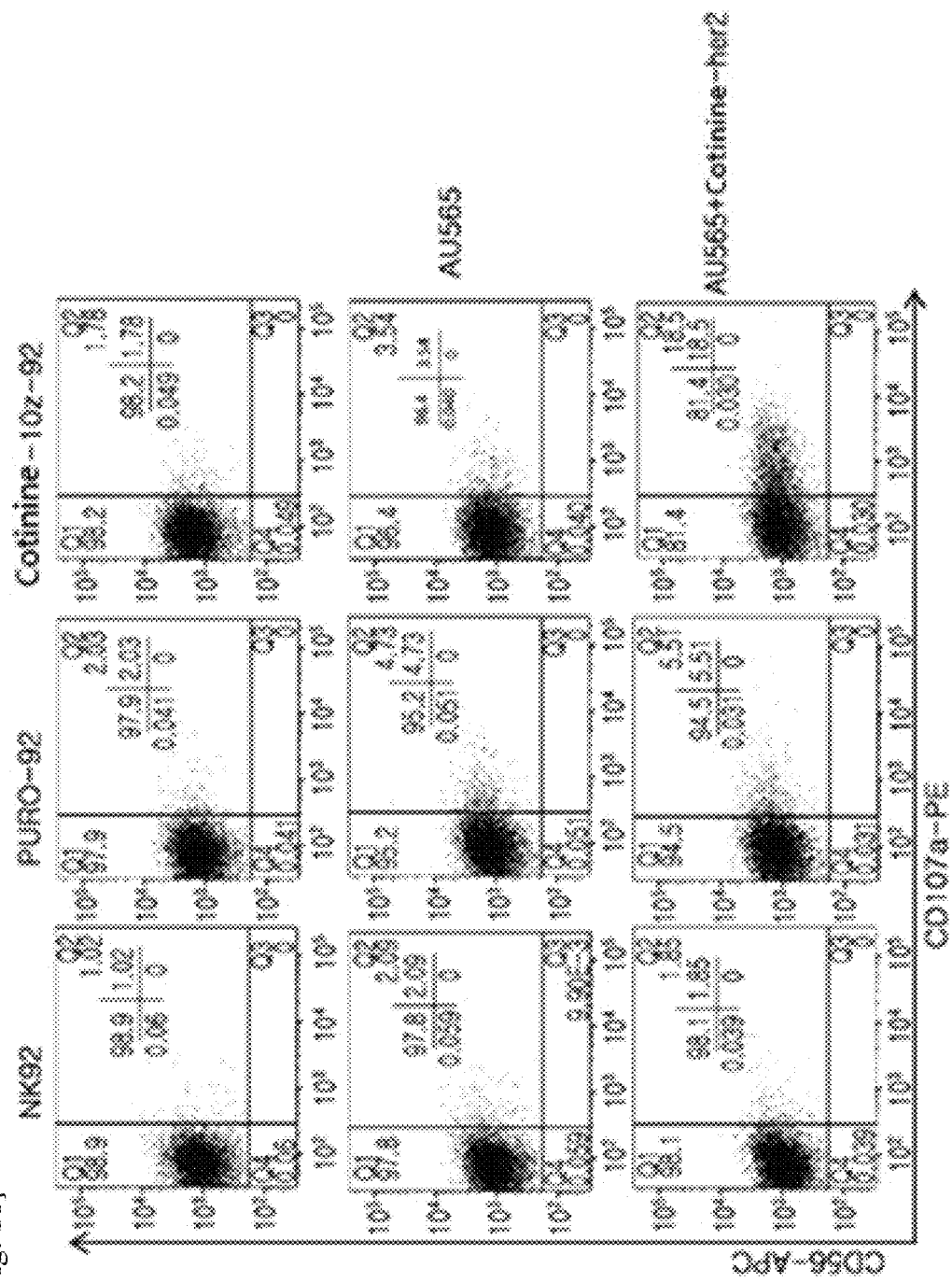
[Fig. 11]

[Fig. 12]
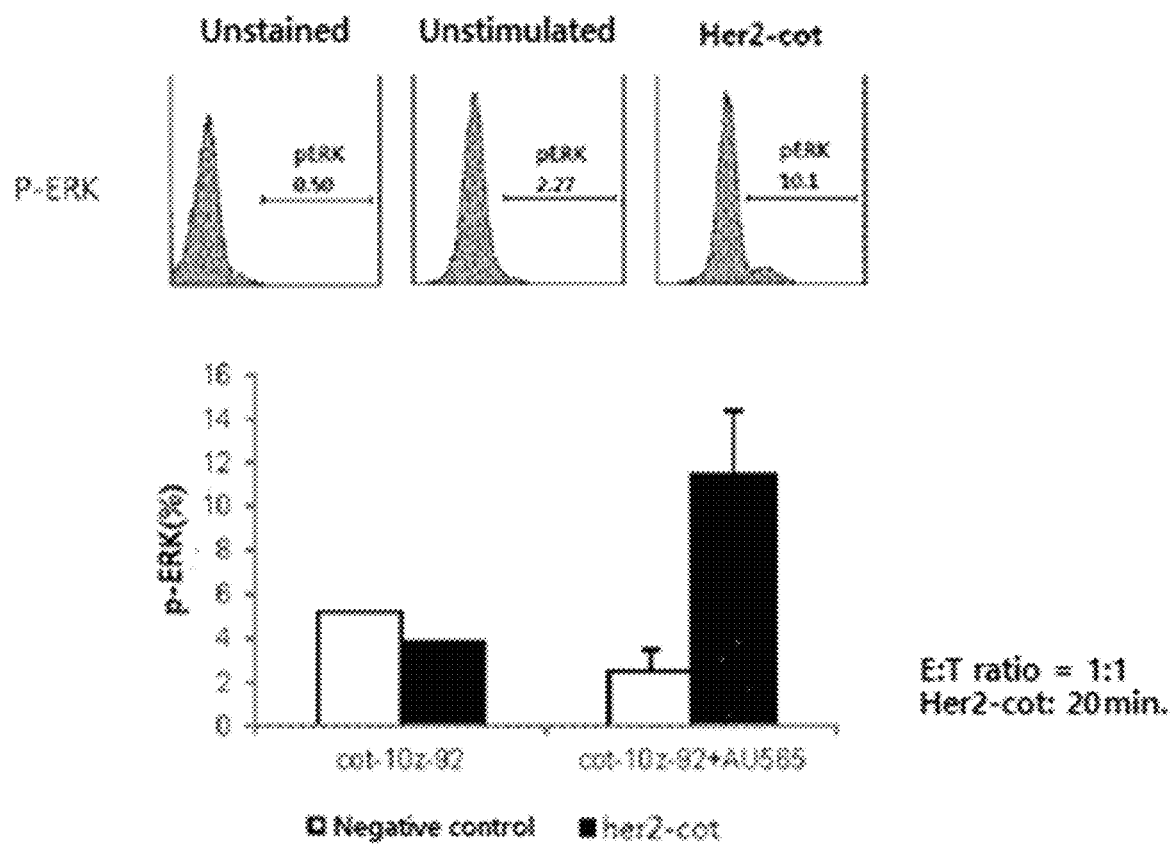

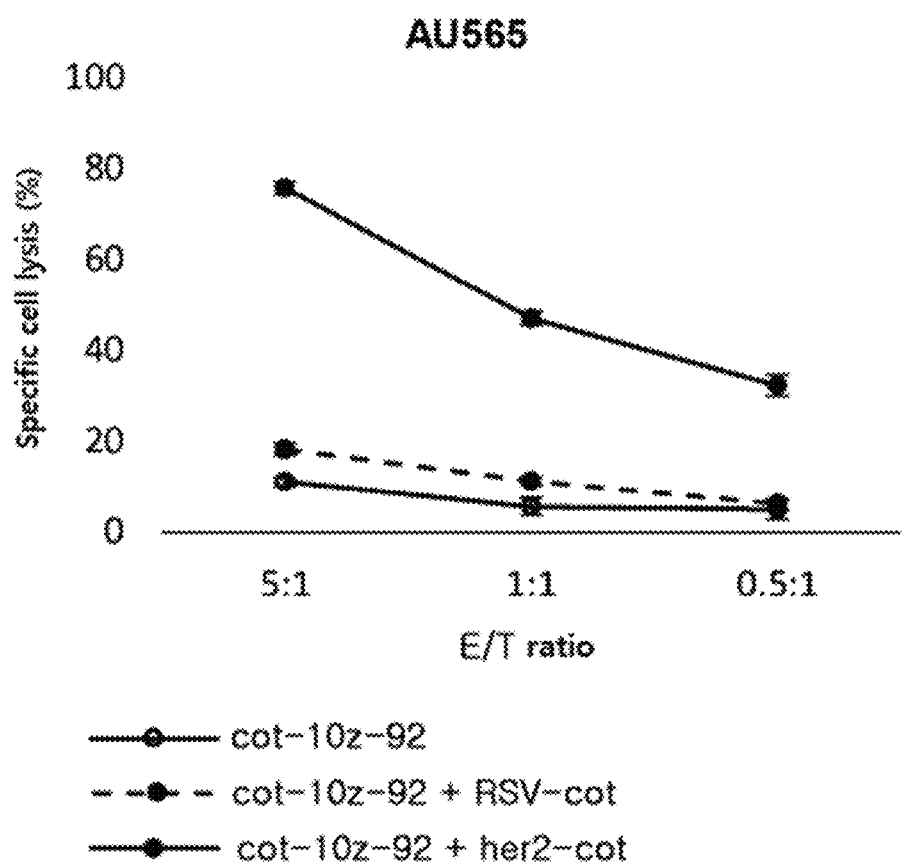
[Fig. 13]

[Fig. 14]
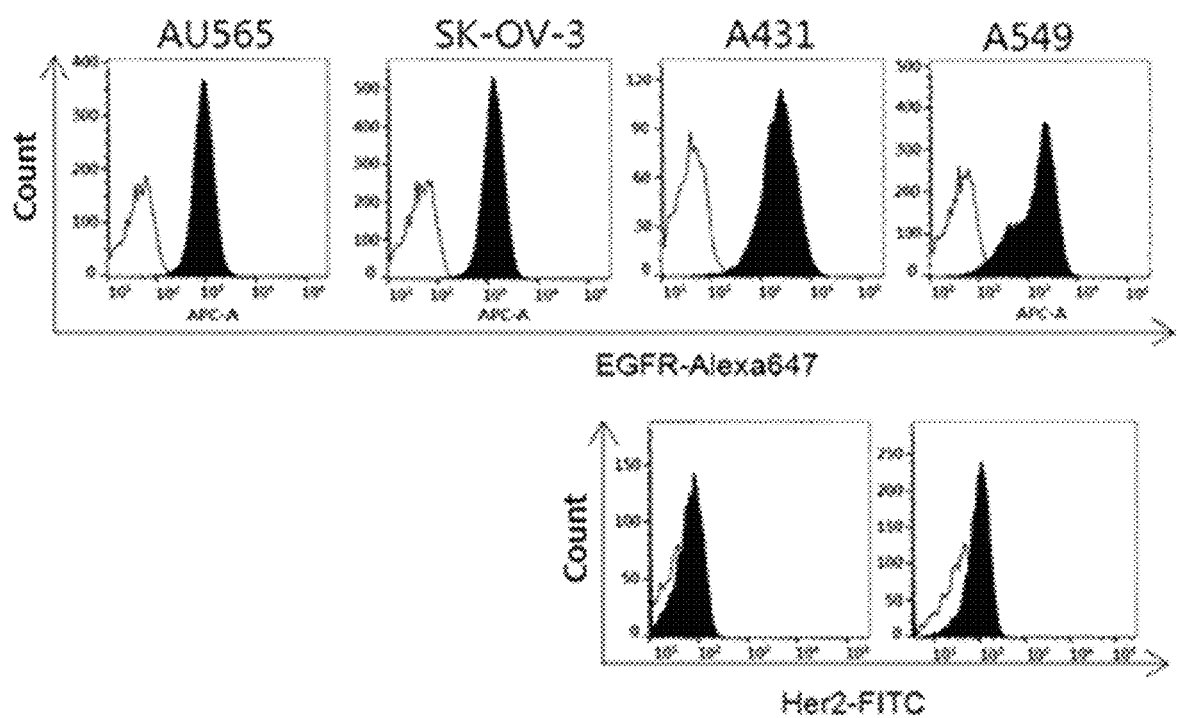

[Fig. 15]
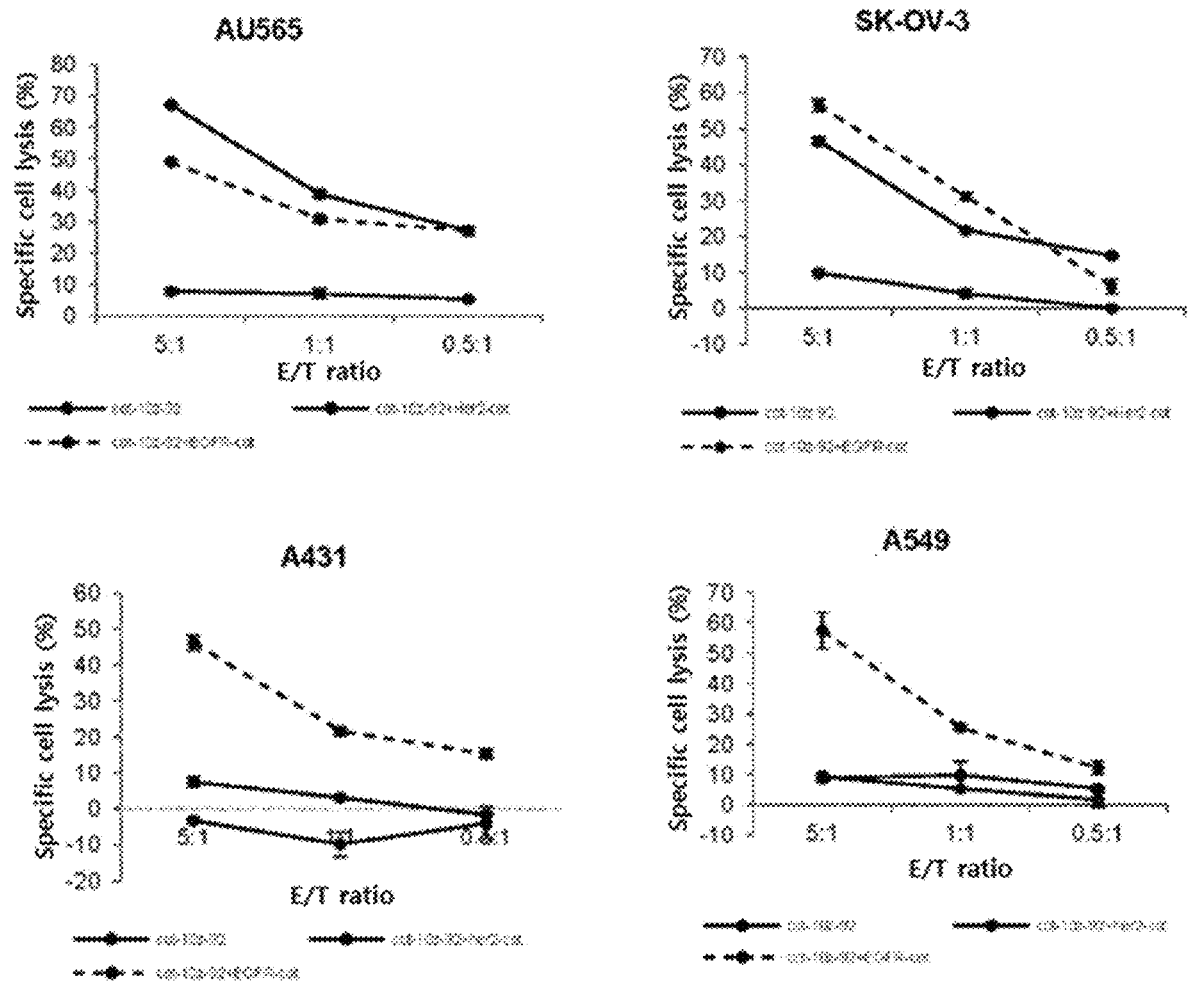

[Fig. 16]
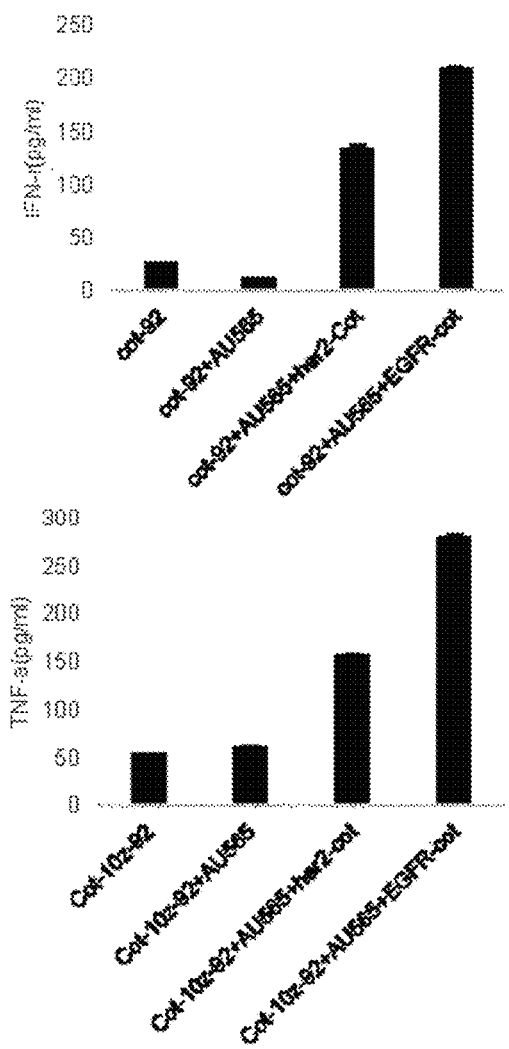
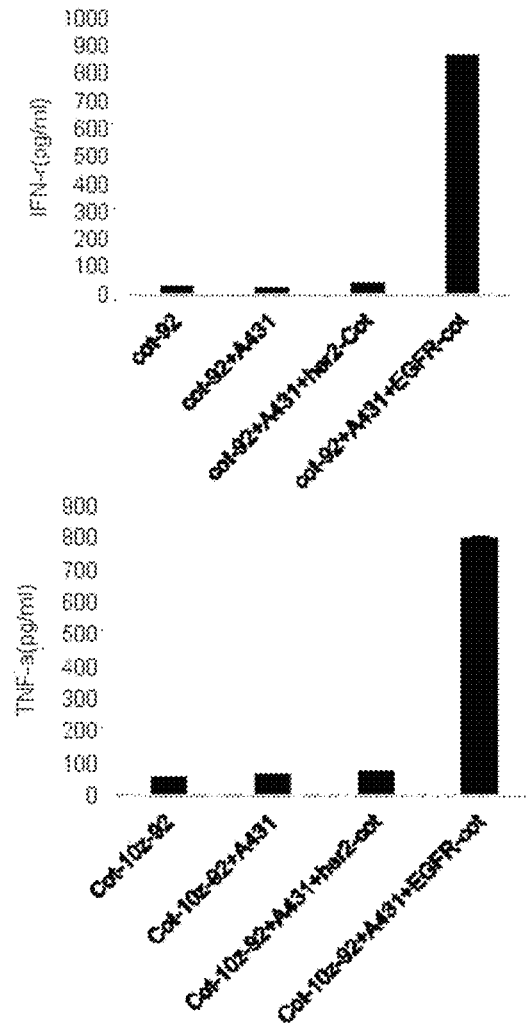

[Fig. 17]
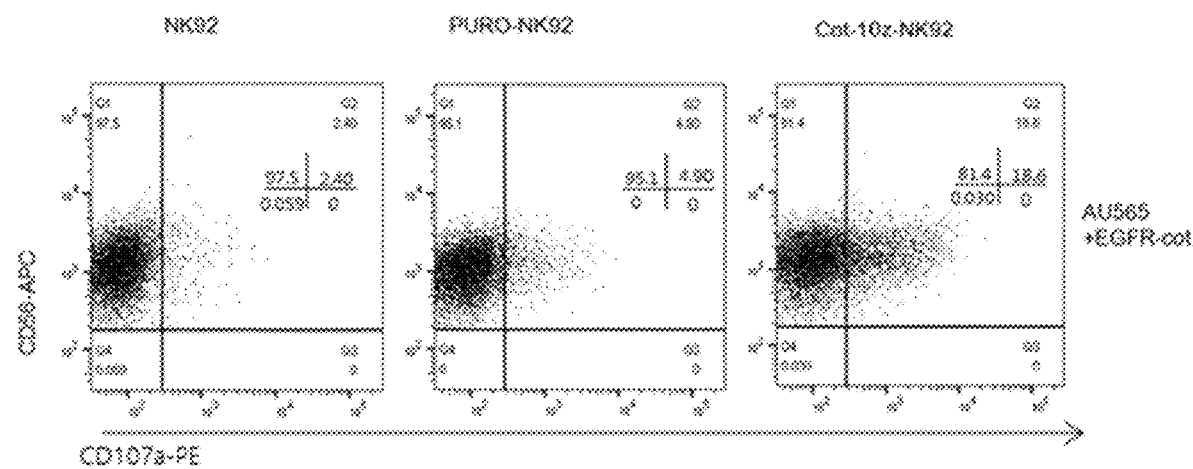

[Fig. 18]
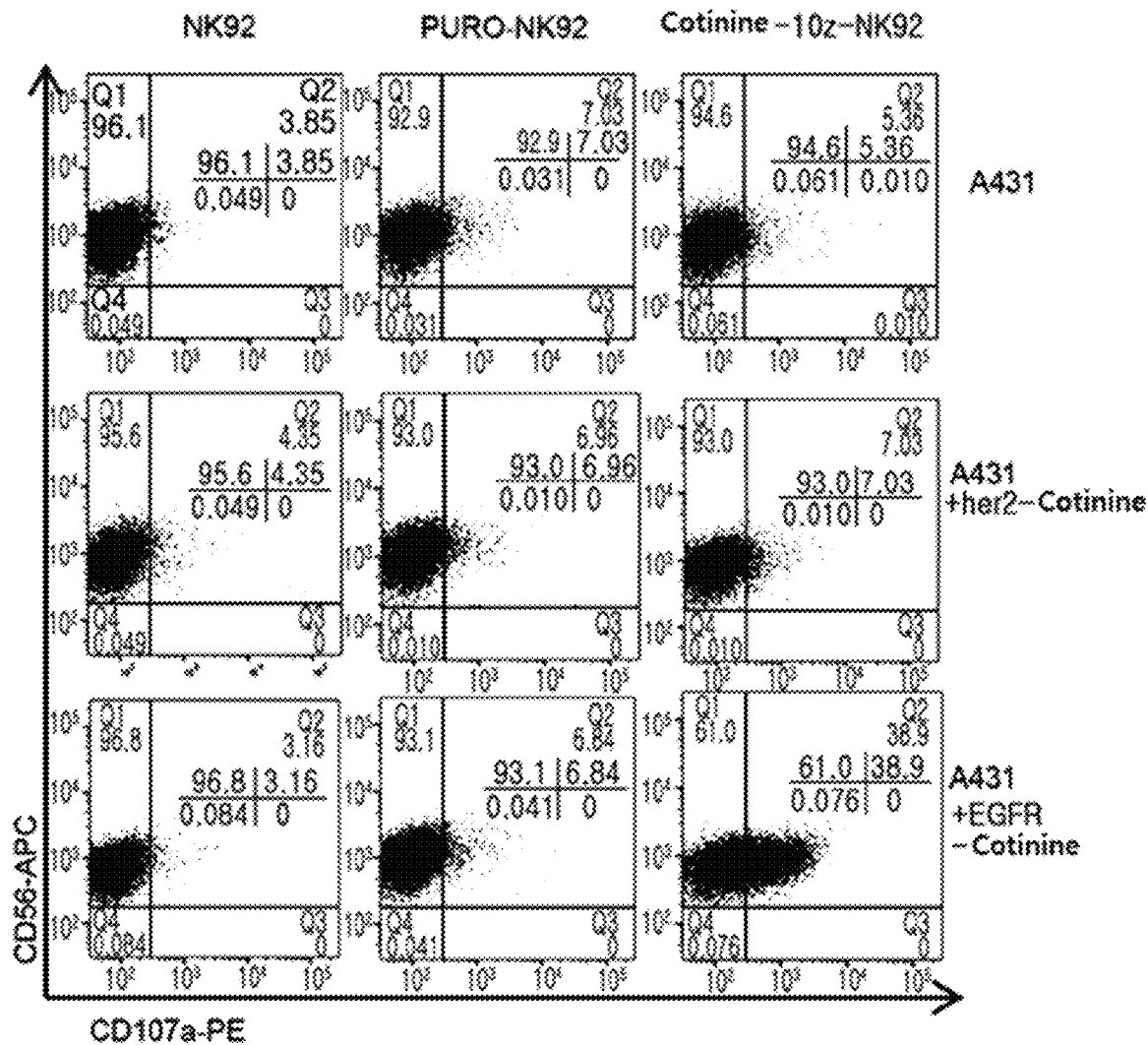

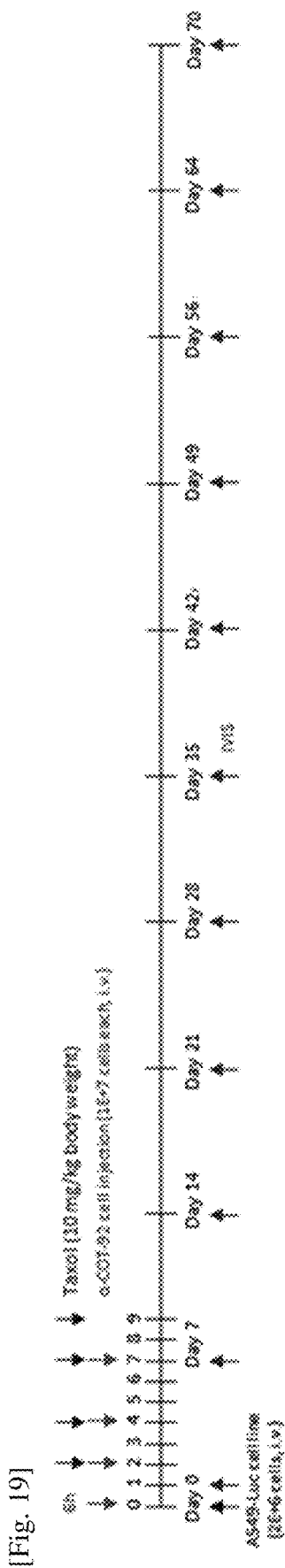
[Fig. 19]

[Fig. 20]
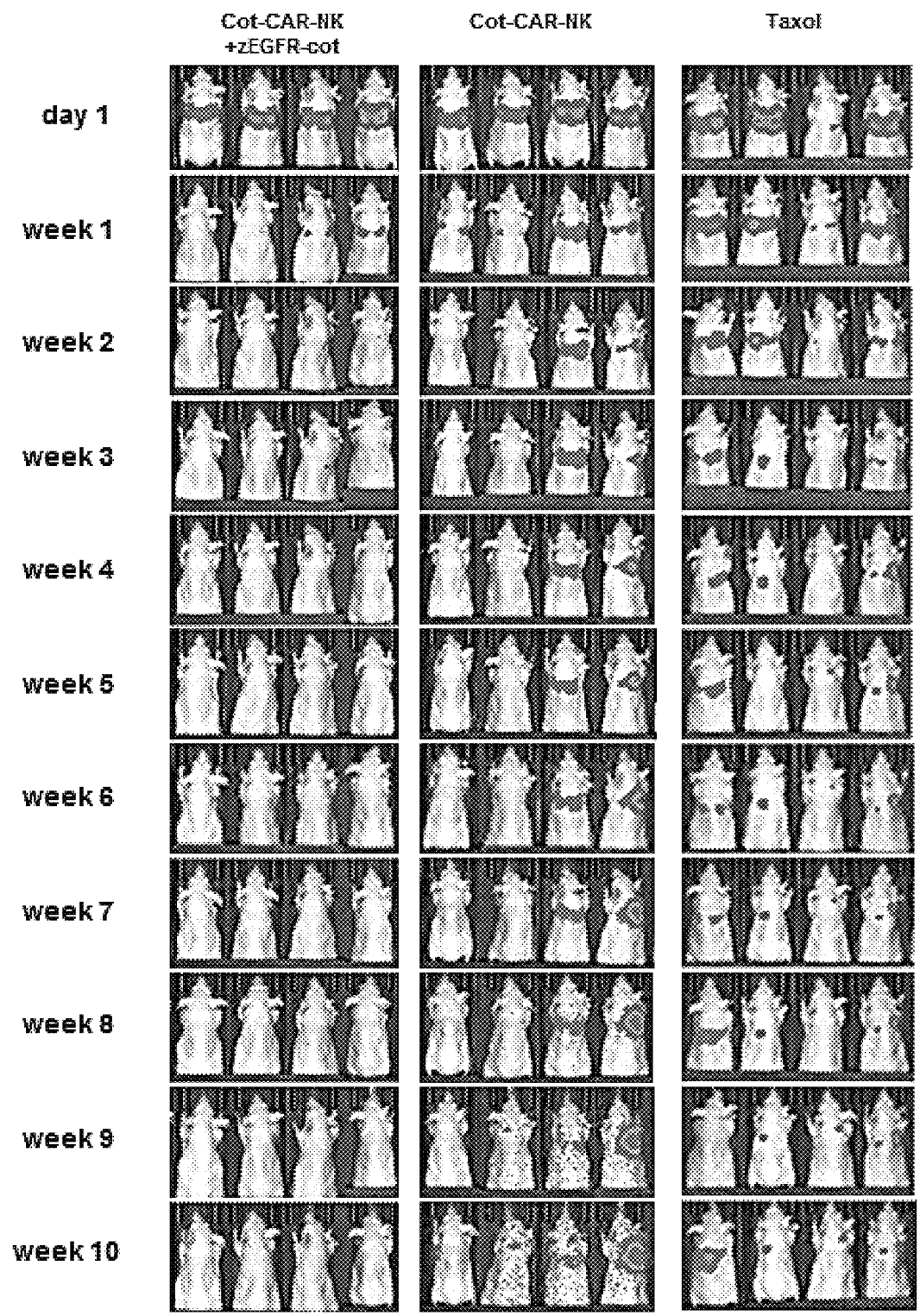

[Fig. 21]
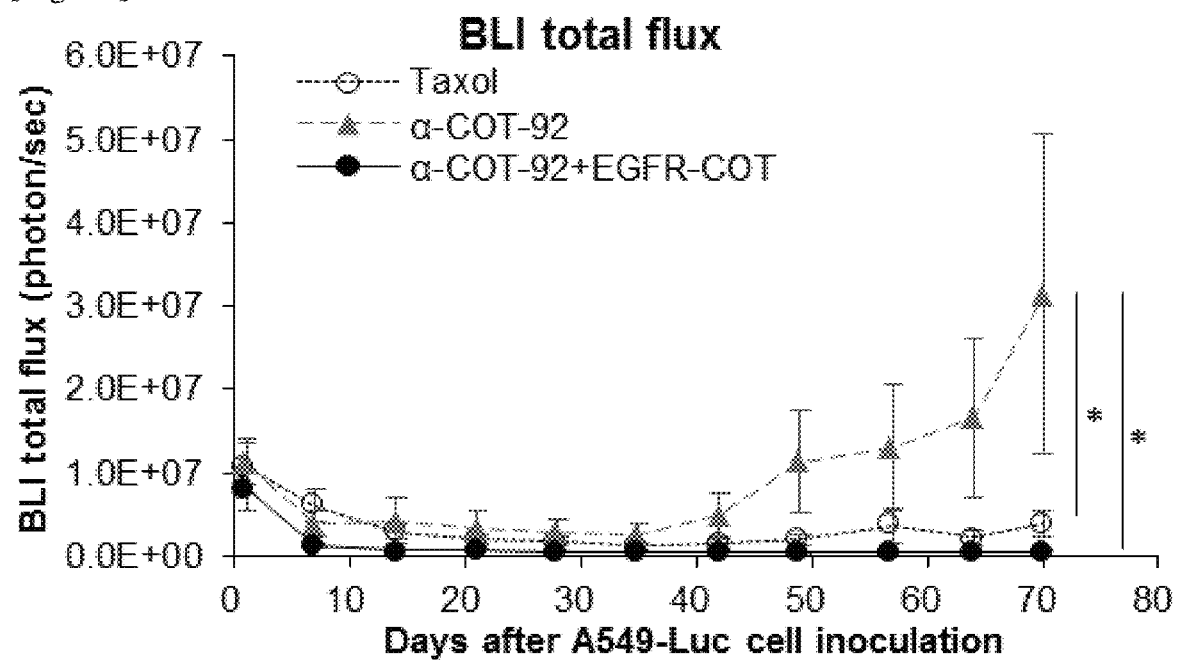

[Fig. 22]
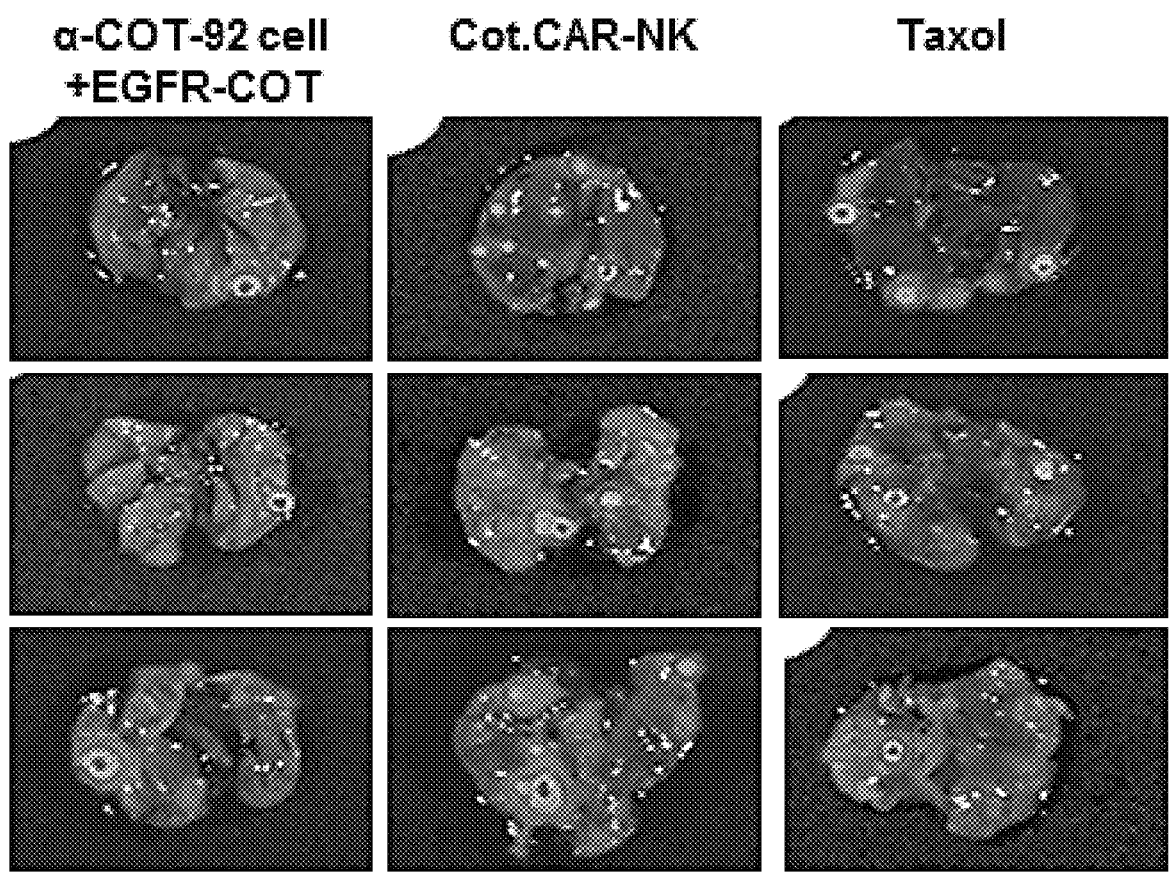

[Fig. 23]
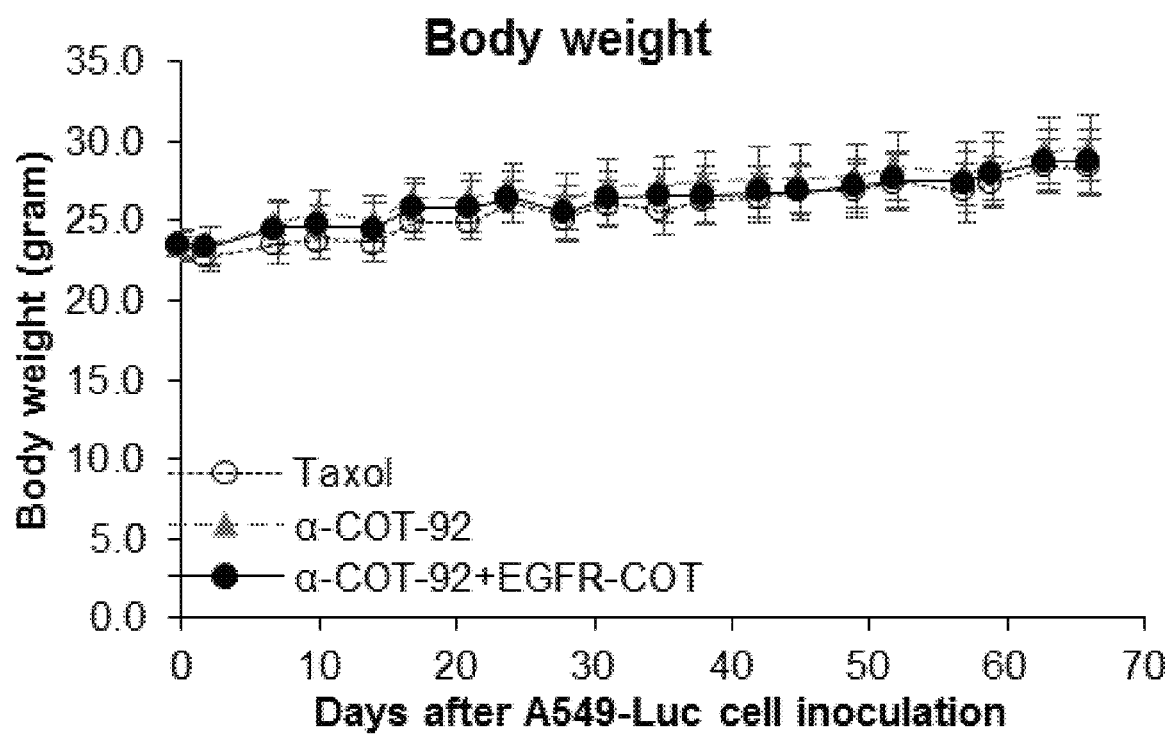

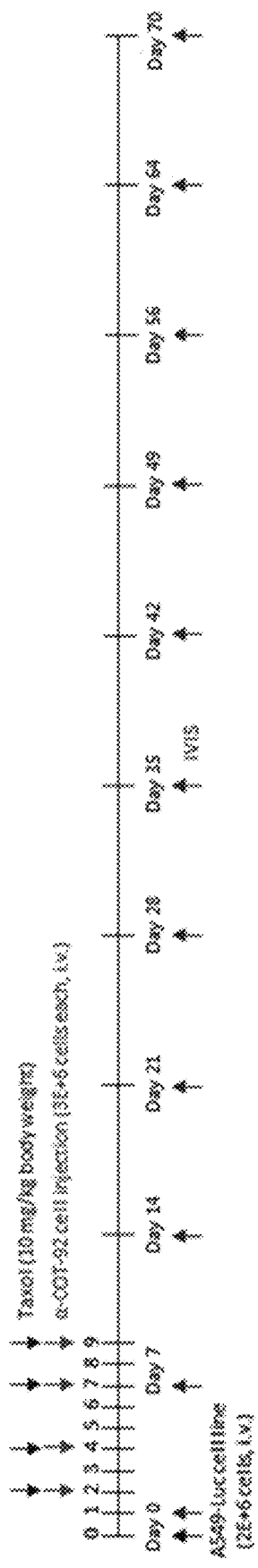
[Fig. 24]

[Fig. 25]
Day 50
PBS
α-COT-92
+EGFR-COT
α-COT-92
α-EGFR-92
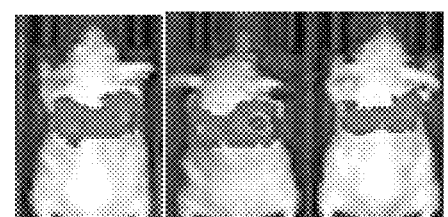
Taxol

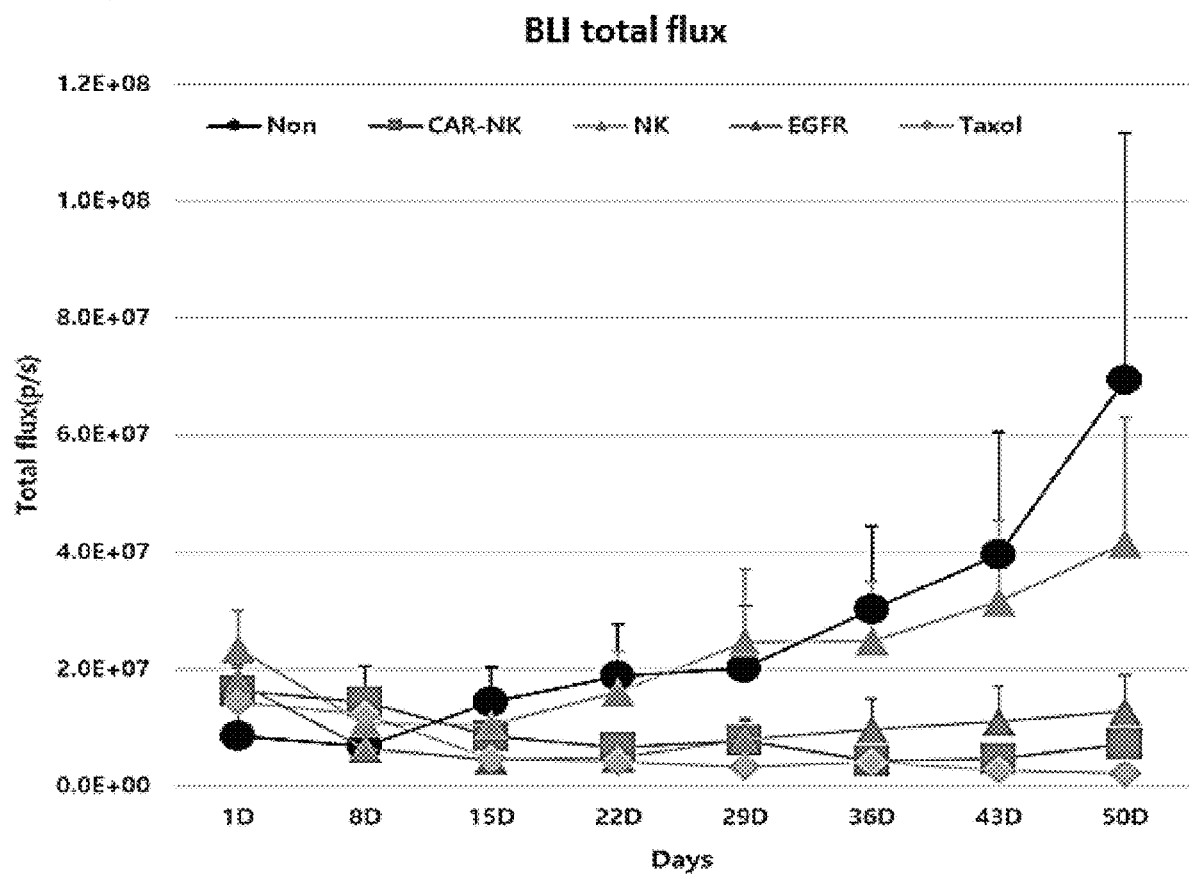
[Fig. 26]

SEQUENCE LISTING

```
<160> NUMBER OF SEQ ID NOS: 30

<210> SEQ ID NO 1
<211> LENGTH: 330
<212> TYPE: DNA
<213> ORGANISM: Artificial Sequence
<220> FEATURE:
<223> OTHER INFORMATION: light variant chain

<400> SEQUENCE: 1
gagctcgatc tgacccagac tccagcctcc gtgtctgcag ctgtgggagg cacagtcacc      60
atcaattgcc agtccagtca gagtccttat agtaacgagt ggttatcctg gtatcagcag     120
aaaccagggc aggctcccaa agtcctaatt tctaggatat ccactctggc atctggggtc     180
tcatcgcggt tcaaaggcag tggatctggg acacagttca ctctcaccat aagcgacctg     240
gagtgtggcg acgctgccac ttatttctgt gcaggcggtt ataatttgg tttgtttcct     300 ttcggcggag ggaccgagct ggagatccta                                      330

<210> SEQ ID NO 2
<211> LENGTH: 360
<212> TYPE: DNA
<213> ORGANISM: Artificial Sequence
<220> FEATURE:
<223> OTHER INFORMATION: heavy variant chain

<400> SEQUENCE: 2
agatcttccc agtcggtgaa ggagtccgag ggtcgcctgg tcacgcctgg aggatccctg      60
acactcacct gcacagtctc tggaatcgac ctcagtaggg actggatgaa ctgggtccgc     120
caggctccag gggaggggct ggaatggatc ggagccattg gtagaagtgg agacacatac     180
tacgcgacct gggcgaaagg ccgattcacc atctccaaaa cctcgtcgag gacggtgact     240
ctaacagtca ccgatctgca gcgctcagac acggccacct atttctgtgc cagaattcct     300
tattttggtt ggaataatgg tgacatctgg ggcccaggca ccctggtcac catctcttca     360

<210> SEQ ID NO 3
<211> LENGTH: 45
<212> TYPE: DNA
<213> ORGANISM: Artificial Sequence
<220> FEATURE:
<223> OTHER INFORMATION: linker

<400> SEQUENCE: 3
tcctctggtg gcggtggctc gggcggtggt ggggtggtt cctct                       45
```

```
<210> SEQ ID NO 4
<211> LENGTH: 203
<212> TYPE: DNA
<213> ORGANISM: Artificial Sequence
<220> FEATURE:
<223> OTHER INFORMATION: Human CD8 hinge region

<400> SEQUENCE: 4
ggggtcaccg tctcttcagc gctgagcaac tccatcatgt acttcagcca cttcgtgccg     60
gtcttcctgc cagcgaagcc caccacgacg ccagcgccgc gaccaccaac accggcgccc    120
accatcgcgt cgcagcccct gtccctgcgc ccagaggcat gccggccagc ggcggggggc    180
gcagtgcaca cgagggggct gga                                             203

<210> SEQ ID NO 5
<211> LENGTH: 252
<212> TYPE: DNA
<213> ORGANISM: Artificial Sequence
<220> FEATURE:
<223> OTHER INFORMATION: CD28

<400> SEQUENCE: 5
gtgaaaggga acacctttg tccaagtccc ctatttcccg gaccttctaa gcccttttgg      60
gtgctggtgg tggttggtgg agtcctggct tgctatagct tgctagtaac agtggccttt    120
attattttct gggtgaggag taagaggagc aggctcctgc acagtgacta catgaacatg    180
actccccgcc gccccgggcc caccgcaag cattaccagc cctatgcccc accacgcgac     240
ttcgcagcct at                                                         252

<210> SEQ ID NO 6
<211> LENGTH: 65
<212> TYPE: DNA
<213> ORGANISM: Artificial Sequence
<220> FEATURE:
<223> OTHER INFORMATION: Human CD8 alpha region

<400> SEQUENCE: 6
atggccttac cagtgaccgc cttgctcctg ccgctggcct tactgctcca cgccgccagg     60
ccggc                                                                 65

<210> SEQ ID NO 7
<211> LENGTH: 30
<212> TYPE: DNA
<213> ORGANISM: Artificial Sequence
<220> FEATURE:
<223> OTHER INFORMATION: Myc epitope

<400> SEQUENCE: 7
gaacaaaaac tcatctcaga agaggatctg                                      30

<210> SEQ ID NO 8
<211> LENGTH: 72
<212> TYPE: DNA
<213> ORGANISM: Artificial Sequence
<220> FEATURE:
<223> OTHER INFORMATION: DAP10

<400> SEQUENCE: 8
ctgtgcgcac gcccacgccg cagccccgcc aagaagatg gcaaagtcta catcaacatg      60
ccaggcaggg gc                                                         72

<210> SEQ ID NO 9
```

<211> LENGTH: 339
<212> TYPE: DNA
<213> ORGANISM: Artificial Sequence
<220> FEATURE:
<223> OTHER INFORMATION: CD3 zeta

<400> SEQUENCE: 9

```
agagtgaagt tcagcaggag cgcagacgcc ccgcgtacc agcagggcca gaaccagctc      60
tataacgagc tcaatctagg acgaagagag gagtacgatg ttttggacaa gacgtggc     120 cgggaccctg agatggggg aaagccgaga aggaagaacc ctcaggaagg cctgtacaat    180
gaactgcaga agataagat ggcggaggcc tacagtgaga ttgggatgaa aggcgagcgc    240 cggagggca agggggcacga tggcctttac cagggtctca gtacagccac caaggacacc    300
tacgacgccc ttcacatgca ggccctgccc cctcgctaa                           339
```

<210> SEQ ID NO 10
<211> LENGTH: 21
<212> TYPE: PRT
<213> ORGANISM: Artificial Sequence
<220> FEATURE:
<223> OTHER INFORMATION: Human CD8 alpha region

<400> SEQUENCE: 10

Met Ala Leu Pro Val Thr Ala Leu Leu Leu Pro Leu Ala Leu Leu Leu
1               5                   10                  15

His Ala Ala Arg Pro
            20

<210> SEQ ID NO 11
<211> LENGTH: 245
<212> TYPE: PRT
<213> ORGANISM: Artificial Sequence
<220> FEATURE:
<223> OTHER INFORMATION: Cotinine-ScFv

<400> SEQUENCE: 11

Glu Leu Asp Leu Thr Gln Thr Pro Ala Ser Val Ser Ala Ala Val Gly
1               5                   10                  15

Gly Thr Val Thr Ile Asn Cys Gln Ser Gln Ser Pro Tyr Ser Asn
            20                  25                  30

Glu Trp Leu Ser Trp Tyr Gln Gln Lys Pro Gly Gln Ala Pro Lys Val
        35                  40                  45

Leu Ile Ser Arg Ile Ser Thr Leu Ala Ser Gly Val Ser Ser Arg Phe
    50                  55                  60

Lys Gly Ser Gly Ser Gly Thr Gln Phe Thr Leu Thr Ile Ser Asp Leu
65                  70                  75                  80

Glu Cys Gly Asp Ala Ala Thr Tyr Phe Cys Ala Gly Gly Tyr Asn Phe
                85                  90                  95

Gly Leu Phe Pro Phe Gly Gly Gly Thr Glu Leu Glu Ile Leu Ser Ser
            100                 105                 110

Gly Gly Gly Gly Ser Gly Gly Gly Gly Ser Ser Arg Ser Ser
        115                 120                 125

Gln Ser Val Lys Glu Ser Glu Gly Arg Leu Val Thr Pro Gly Gly Ser
    130                 135                 140

Leu Thr Leu Thr Cys Thr Val Ser Gly Ile Asp Leu Ser Arg Asp Trp
145                 150                 155                 160

Met Asn Trp Val Arg Gln Ala Pro Gly Glu Gly Leu Glu Trp Ile Gly
                165                 170                 175

-continued

```
Ala Ile Gly Arg Ser Gly Asp Thr Tyr Tyr Ala Thr Trp Ala Lys Gly
            180                 185                 190

Arg Phe Thr Ile Ser Lys Thr Ser Arg Thr Val Thr Leu Thr Val
        195                 200                 205

Thr Asp Leu Gln Arg Ser Asp Thr Ala Thr Tyr Phe Cys Ala Arg Ile
    210                 215                 220

Pro Tyr Phe Gly Trp Asn Asn Gly Asp Ile Trp Gly Pro Gly Thr Leu
225                 230                 235                 240

Val Thr Ile Ser Ser
            245

<210> SEQ ID NO 12
<211> LENGTH: 67
<212> TYPE: PRT
<213> ORGANISM: Artificial Sequence
<220> FEATURE:
<223> OTHER INFORMATION: Human CD8 hinge region

<400> SEQUENCE: 12

Gly Val Thr Val Ser Ser Ala Leu Ser Asn Ser Ile Met Tyr Phe Ser
1               5                   10                  15

His Phe Val Pro Val Phe Leu Pro Ala Lys Pro Thr Thr Thr Pro Ala
            20                  25                  30

Pro Arg Pro Pro Thr Pro Ala Pro Thr Ile Ala Ser Gln Pro Leu Ser
        35                  40                  45

Leu Arg Pro Glu Ala Cys Arg Pro Ala Ala Gly Gly Ala Val His Thr
    50                  55                  60

Arg Gly Leu
65

<210> SEQ ID NO 13
<211> LENGTH: 10
<212> TYPE: PRT
<213> ORGANISM: Artificial Sequence
<220> FEATURE:
<223> OTHER INFORMATION: Myc epitope

<400> SEQUENCE: 13

Glu Gln Lys Leu Ile Ser Glu Glu Asp Leu
1               5                   10

<210> SEQ ID NO 14
<211> LENGTH: 24
<212> TYPE: PRT
<213> ORGANISM: Artificial Sequence
<220> FEATURE:
<223> OTHER INFORMATION: Dap10

<400> SEQUENCE: 14

Leu Cys Ala Arg Pro Arg Arg Ser Pro Ala Gln Glu Asp Gly Lys Val
1               5                   10                  15

Tyr Ile Asn Met Pro Gly Arg Gly
            20

<210> SEQ ID NO 15
<211> LENGTH: 112
<212> TYPE: PRT
<213> ORGANISM: Artificial Sequence
<220> FEATURE:
<223> OTHER INFORMATION: CD3 zeta

<400> SEQUENCE: 15
```

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 16
<211> LENGTH: 84
<212> TYPE: PRT
<213> ORGANISM: Artificial Sequence
<220> FEATURE:
<223> OTHER INFORMATION: CD28

<400> SEQUENCE: 16

```
Val Lys Gly Lys His Leu Cys Pro Ser Pro Leu Phe Pro Gly Pro Ser
1               5                   10                  15

Lys Pro Phe Trp Val Leu Val Val Gly Gly Val Leu Ala Cys Tyr
            20                  25                  30

Ser Leu Leu Val Thr Val Ala Phe Ile Ile Phe Trp Val Arg Ser Lys
        35                  40                  45

Arg Ser Arg Leu Leu His Ser Asp Tyr Met Asn Met Thr Pro Arg Arg
50                  55                  60

Pro Gly Pro Thr Arg Lys His Tyr Gln Pro Tyr Ala Pro Pro Arg Asp
65                  70                  75                  80

Phe Ala Ala Tyr
```

<210> SEQ ID NO 17
<211> LENGTH: 735
<212> TYPE: DNA
<213> ORGANISM: Artificial Sequence
<220> FEATURE:
<223> OTHER INFORMATION: Cotinine-scFv

<400> SEQUENCE: 17
gagctcgatc tgacccagac tccagcctcc gtgtctgcag ctgtgggagg cacagtcacc       60
atcaattgcc agtccagtca gagtccttat agtaacgagt ggttatcctg gtatcagcag      120
aaaccagggc aggctcccaa agtcctaatt tctaggatat ccactctggc atctggggtc      180
tcatcgcggt tcaaaggcag tggatctggg acacagttca ctctcaccat aagcgacctg      240
gagtgtggcg acgctgccac ttatttctgt gcaggcggtt ataattttgg tttgtttcct      300
ttcggcggag ggaccgagct ggagatccta tcctctggtg gcggtggctc gggcggtggt      360
gggggtggtt cctctagatc ttcccagtcg gtgaaggagt ccgagggtcg cctggtcacg      420
cctggaggat ccctgacact cacctgcaca gtctctggaa tcgacctcag tagggactgg      480
atgaactggg tccgccaggc tccaggggag gggctggaat ggatcggagc cattggtaga      540
agtggagaca catactacgc gacctggcg aaaggccgat tcaccatctc caaaacctcg       600
tcgaggacgg tgactctaac agtcaccgat ctgcagcgct cagacacggc cacctatttc      660
```

```
tgtgccagaa ttccttattt tggttggaat aatggtgaca tctggggccc aggcaccctg    720
gtcaccatct cttca                                                     735
```

<210> SEQ ID NO 18
<211> LENGTH: 75
<212> TYPE: DNA
<213> ORGANISM: Artificial Sequence
<220> FEATURE:
<223> OTHER INFORMATION: signal peptide forward primer

<400> SEQUENCE: 18

```
ctcgaggcca ggatggcctt accagtgacc gccttgctcc tgccgctggc cttgctgctc    60
cacgccgcca ggccg                                                    75
```

<210> SEQ ID NO 19
<211> LENGTH: 39
<212> TYPE: DNA
<213> ORGANISM: Artificial Sequence
<220> FEATURE:
<223> OTHER INFORMATION: signal peptide reverse primer

<400> SEQUENCE: 19

```
agatctttag cgaggggggca gggcctcccc ctcgtgtgc                          39
```

<210> SEQ ID NO 20
<211> LENGTH: 34
<212> TYPE: DNA
<213> ORGANISM: Artificial Sequence
<220> FEATURE:
<223> OTHER INFORMATION: Myc epitope forward primer

<400> SEQUENCE: 20

```
ggcccgggag gccgcgaaca aaaactcatc tcag                                34
```

<210> SEQ ID NO 21
<211> LENGTH: 18
<212> TYPE: DNA
<213> ORGANISM: Artificial Sequence
<220> FEATURE:
<223> OTHER INFORMATION: Myc epitope reverse primer

<400> SEQUENCE: 21

```
aagcttcaga tcctcttc                                                  18
```

<210> SEQ ID NO 22
<211> LENGTH: 26
<212> TYPE: DNA
<213> ORGANISM: Artificial Sequence
<220> FEATURE:
<223> OTHER INFORMATION: Human CD8 hinge region forward primer

<400> SEQUENCE: 22

```
aagcttgggg tcaccgtctc ttcagc                                         26
```

<210> SEQ ID NO 23
<211> LENGTH: 25
<212> TYPE: DNA
<213> ORGANISM: Artificial Sequence
<220> FEATURE:
<223> OTHER INFORMATION: Human CD8 hinge region reverse primer

<400> SEQUENCE: 23

```
aagcttatcc agccccctcg tgtgc                                          25
```

<210> SEQ ID NO 24
<211> LENGTH: 31
<212> TYPE: DNA
<213> ORGANISM: Artificial Sequence
<220> FEATURE:
<223> OTHER INFORMATION: CD28 forward primer

<400> SEQUENCE: 24
cgcggatccg tgaaagggaa acacctttgt c                          31

<210> SEQ ID NO 25
<211> LENGTH: 27
<212> TYPE: DNA
<213> ORGANISM: Artificial Sequence
<220> FEATURE:
<223> OTHER INFORMATION: CD28 reverse primer

<400> SEQUENCE: 25
ccggaattca taggctgcga agtcgcg                               27

<210> SEQ ID NO 26
<211> LENGTH: 27
<212> TYPE: DNA
<213> ORGANISM: Artificial Sequence
<220> FEATURE:
<223> OTHER INFORMATION: DAP10 forward primer

<400> SEQUENCE: 26
ccggaattcc tgtgcgcacg cccacgc                               27

<210> SEQ ID NO 27
<211> LENGTH: 37
<212> TYPE: DNA
<213> ORGANISM: Artificial Sequence
<220> FEATURE:
<223> OTHER INFORMATION: DAP10 reverse primer

<400> SEQUENCE: 27
ataagaatgc ggccgcgccc ctgcctggca tgttgat                    37

<210> SEQ ID NO 28
<211> LENGTH: 39
<212> TYPE: DNA
<213> ORGANISM: Artificial Sequence
<220> FEATURE:
<223> OTHER INFORMATION: CD3 zeta forward primer

<400> SEQUENCE: 28
ataagaatgc ggccgctaga gtgaagttca gcaggagcg                  39

<210> SEQ ID NO 29
<211> LENGTH: 30
<212> TYPE: DNA
<213> ORGANISM: Artificial Sequence
<220> FEATURE:
<223> OTHER INFORMATION: CD3 zeta reverse primer

<400> SEQUENCE: 29
tgctctagag cattagcgag ggggcagggc                            30

<210> SEQ ID NO 30
<211> LENGTH: 58
<212> TYPE: PRT
<213> ORGANISM: Artificial Sequence
<220> FEATURE:
<223> OTHER INFORMATION: Anti-EGFR affibody

```
<400> SEQUENCE: 30

Val Asp Asn Lys Phe Asn Lys Glu Met Trp Ala Ala Trp Glu Glu Ile
1               5                   10                  15

Arg Asn Leu Pro Asn Leu Asn Gly Trp Gln Met Thr Ala Phe Ile Ala
            20                  25                  30

Ser Leu Val Asp Asp Pro Ser Gln Ser Ala Asn Leu Leu Ala Glu Ala
        35                  40                      45

Lys Lys Leu Asn Asp Ala Gln Ala Pro Lys
50                      55
```

NATURAL KILLER CELL EXPRESSING ANTI-COTININE CHIMERIC ANTIGEN RECEPTOR

CROSS REFERENCE TO RELATED APPLICATIONS

This application is a Continuation-in-part based on International Application No. PCT/KR2018/000310, filed on Jan. 5, 2018, which claims priority from Korean Patent Application No. 10-2017-0001951, filed on Jan. 5, 2017, and Korean Patent Application No. 10-2017-0001976, filed on Jan. 5, 2017.

SEQUENCE LISTING

The content of the electronically submitted sequence listing, file name: Sequence_Listing_As_Filed.txt; size: 13,804 bytes; and date of creation: Mar. 22, 2022, filed herewith, is incorporated herein by reference in its entirety.

PARTIES TO A JOINT RESEARCH AGREEMENT

The subject matter disclosed in U.S. Pat. No. 11,478,555 (U.S. application Ser. No. 15/753,212) was developed by and the claimed invention was made by or on behalf of, one or more parties to a joint research agreement that was in effect on or before the effective filing date the claimed invention, and the claimed invention was made as a result of activities undertaken within the scope of the joint research agreement. The parties to the joint research agreement are KOREA RESEARCH INSTITUTE OF BIOSCIENCE AND BIOTECHNOLOGY and SEOUL NATIONAL UNIVERSITY R&DB FOUNDATION.

TECHNICAL FIELD

The present invention relates to a natural killer cell expressing an anti-cotinine chimeric antigen receptor (CAR) that specifically binds to cotinine, and a cell therapeutic agent comprising the same.

BACKGROUND ART

Methods of treating cancer have been steadily changing and evolving for decades. From the 1800s to the 1900s, methods such as surgery, chemotherapy, and radiation therapy were mainly carried out, and limitations therewith began to emerge. Most typically, existing therapeutic methods are effective only in the early stage of cancer when metastasis has not occurred; and in a case where metastasis has already occurred, there is a high likelihood of recurrence even after surgery. In addition, it has been reported that chemotherapy has a low therapeutic effect in solid tumors and causes a side effect that growth of normal cells other than cancer cells is also inhibited. Recently, in order to overcome such problems, researches on anti-cancer immunotherapy are actively underway. The anti-cancer immunotherapy refers to causing increased immune reaction so that patients themselves can combat cancer cells.

Recently, there has been a growing interest in cell therapeutic methods which are immune cell therapies and in which immune cells in the body are taken out, potentiated or genetically modified, and introduced again. Typical examples thereof include tumor infiltrating lymphocyte (TIL), chimeric antigen receptor (CAR), and T-cell receptor (TCR) techniques. Among these, researches using the artificial receptor CAR obtained by using genetic recombination/modification have been actively conducted.

Chimeric antigen receptors (CARs) are artificial receptors designed to deliver antigen specificity to T cells. These receptors include antigen-specific components, transmembrane components, and intracellular components which are selected to activate T cells and provide specific immunity. Chimeric antigen receptor-expressing T cells may be used in various therapies including cancer therapy.

Therapeutic agents such as CAR-T are effective against tumors. However, in some cases, these treatments have caused side effects due to partial non-specific attacks on healthy tissues. In order to overcome this problem, researches on the third generation CAR-T are currently underway, and such researches are characterized in that two signal domains serving as a co-stimulatory signal and an artificial receptor (additional engineered receptor) are added to increase a 'cancer cell antigen-recognizing ability' so that side effects of attacking normal cells are minimized. Nevertheless, development of CAR-T cell therapeutic agents is hampered due to the following problems: Current CAR-T techniques have limitations that CAR-T is produced to recognize only one protein expressed in cancer cells, and thus too many costs are required to develop individual therapeutic agents; once CAR-T is injected, toxic T cells continue to function and cause toxicity even after cancer cells have been removed; and in a case where there are normal cells presenting a target protein, CAR-T induces a non-specific attack thereon to cause a fatal side effect which is not reversible.

Therefore, researches on a new improved cell therapeutic agent capable of solving the above problems are urgently needed.

DISCLOSURE OF INVENTION

Technical Problem

As a result of studies to solve the problems of conventional therapeutic agents, the present inventors have produced a natural killer cell expressing a chimeric antigen receptor which uses an antigen-binding domain that specifically binds to cotinine. By doing so, the present inventors have identified that the natural killer cell makes it possible to solve the problems of existing CAR-T therapeutic agents and at the same time to easily develop general-purpose therapeutic agents, and thus has completed the present invention.

Accordingly, an object of the present invention is to provide a cell therapeutic agent which uses a natural killer cell expressing an antigen binding domain that specifically binds to cotinine, and a method for treating cancer using the same.

Solution to Problem

In order to solve the above problems, the present invention provides a natural killer cell where a chimeric antigen receptor (CAR) is expressed, wherein the chimeric antigen receptor includes 1) an antigen binding domain, 2) a transmembrane domain, and 3) an intracellular signaling domain, and the antigen binding domain is a domain that specifically binds to cotinine.

In addition, the present invention provides a cell therapeutic agent, comprising the natural killer cell.

In addition, the present invention provides a pharmaceutical composition for the prevention or treatment of cancer, comprising the natural killer cell as an active ingredient.

In addition, the present invention provides a method for preventing or treating cancer, comprising a step of administering the natural killer cell to a subject.

In addition, the present invention provides a pharmaceutical composition for the diagnosis of cancer, comprising the natural killer cell as an active ingredient.

In addition, the present invention provides a diagnostic kit for cancer, comprising the natural killer cell.

Advantageous Effects of Invention

The natural killer cell expressing the chimeric antigen receptor that specifically binds to cotinine according to the present invention can effectively move to a tumor tissue, regardless of the type of cancer, depending on a binding substance conjugated to cotinine. Accordingly, the natural killer cell according to the present invention can be usefully used as a gene therapeutic method that exhibits an anti-cancer effect with high efficiency.

BRIEF DESCRIPTION OF DRAWINGS

FIG. 1 illustrates pLVX-AcGFP-C1 vector used in the present invention.

FIG. 2 illustrates a schematic diagram of a cotinine-specific CAR-NK cell and an exemplary cotinine conjugate.

FIG. 3 illustrates action of Cot-CAR-NK cell, which is a cotinine-specific NK cell.

FIG. 4 illustrates a specific related sequence used in the present invention.

FIG. 5 illustrates an exemplary schematic diagram of an anti-cotinine chimeric antigen receptor and an expression system thereof.

FIG. 6 illustrates results obtained by measuring, with flow cytometry, expression of CAR in NK92 cells.

FIG. 7 illustrates a result confirming binding specificity of Cot-CAR-NK to cotinine of cotinine conjugate.

FIG. 8 illustrates results confirming, with flow cytometry, an expression level of Her2 for various cancer cells.

FIG. 9 illustrates results confirming, through the calcein-AM method, a cell killing effect of the cotinine-CAR NK92 cell of the present invention depending on the presence or absence of a Her2-cotinine conjugate.

FIG. 10 illustrates results confirming, through ELISA, secretion levels of cytokines in the cotinine-CAR NK92 cell.

FIG. 11 illustrates results confirming, with flow cytometry, an expression level of CD107a in cells.

FIG. 12 illustrates results confirming, with flow cytometry, phosphorylation of Erk through the endo domain of the cotinine-CAR NK92.

FIG. 13 illustrates a result confirming a cell killing effect of the cotinine-CAR NK cell depending on a binding substance of the cotinine conjugate.

FIG. 14 illustrates results confirming, with flow cytometry, expression levels of Her2 and EGFR in AU565, SK-OV-3, A431, and A459 cells.

FIG. 15 illustrates results confirming, through the calcein-AM method, a cell killing effect of the cotinine-CAR NK cell on various cancer cells depending on a cotinine conjugate.

FIG. 16 illustrates results confirming, through ELISA, changes in cytokine secretion in cancer cells depending on treatment with the cotinine-CAR NK92 and a conjugate.

FIG. 17 illustrates results confirming CD107a expression of the cot-CAR-NK cell depending on the presence or absence of the cotinine conjugate when the cotinine-CAR-NK cell is mixed with AU565 cells.

FIG. 18 illustrates results confirming CD107a expression of the cot-CAR-NK cell depending on the presence or absence of the cotinine conjugate when the cotinine-CAR-NK cell is mixed with A431 cells.

FIG. 19 illustrates an experimental schedule for checking an anti-cancer effect of the cotinine antigen receptor in a lung cancer metastasis model.

FIG. 20 illustrates results confirming, through bioluminescent images, anti-cancer effects of a Taxol-treated group (positive control), a cotinine-CAR-NK-treated group, and a cotinine-CAR-NK and zEGFR-COT-treated group (Cot-CAR-NK+zEGFR-cot) in development and metastasis of lung cancer.

FIG. 21 graphically illustrates the mean value of the total flux for bioluminescence measured in the three groups (Taxol-treated group, cotinine-CAR-NK-treated group, and cotinine-CAR-NK and zEGFR-COT-treated group).

FIG. 22 illustrates results obtained by sacrificing mice for which 70 days has elapsed since treatment with Taxol, cotinine-CAR-NK, or cotinine-CAR-NK and zEGFR-COT, extracting the lungs therefrom, and then confirming nodules formed in the lungs through bioluminescence images.

FIG. 23 illustrates the mean body weight of mice in the three groups (Taxol-treated group, cotinine-CAR-NK-treated group, and cotinine-CAR-NK and zEGFR-COT-treated group) during the administration and observation schedule.

FIG. 24 illustrates an experimental schedule for checking an anti-cancer effect of the cotinine antigen receptor in a lung cancer metastasis model.

FIG. 25 illustrates results confirming, through bioluminescent images, anti-cancer effects of a negative control (PBS), a positive control group (Taxol), a cotinine-CAR-NK-treated group, a cotinine-CAR-NK and zEGFR-COT-treated group, and a zEGFR-CAR-NK-treated group in a lung cancer development and growth inhibition model.

FIG. 26 graphically illustrates the mean value of the total flux for bioluminescence measured in the five groups (negative control (PBS), positive control group (Taxol), cotinine-CAR-NK-treated group, cotinine-CAR-NK and zEGFR-COT-treated group, and zEGFR-CAR-NK-treated group).

BEST MODE FOR CARRYING OUT THE INVENTION

Hereinafter, the present invention will be described in detail.

In an aspect of the present invention, there is provided a natural killer cell where a chimeric antigen receptor (CAR) is expressed, wherein the chimeric antigen receptor includes 1) an antigen binding domain, 2) a transmembrane domain, and 3) an intracellular signaling domain, and the antigen binding domain is a domain that specifically binds to cotinine.

The natural killer cell expressing the chimeric antigen receptor that specifically binds to cotinine according to the present invention can effectively move to a tumor tissue, regardless of the type of cancer, depending on a binding substance conjugated to cotinine. Accordingly, the natural killer cell according to the present invention can be usefully used as a gene therapeutic method that exhibits an anti-cancer effect with high efficiency.

Since the natural killer cell expressing the chimeric antigen receptor according to the present invention is characterized by specifically binding to cotinine, it includes an antigen binding domain that specifically binds to cotinine.

The antigen binding domain may be an antibody or antibody fragment which specifically binds to cotinine. The NK cell expressing the chimeric antigen receptor may be administered to a patient together with a conjugate fused with cotinine to treat cancer.

Particularly, the natural killer cell (CAR-NK cell) expressing the chimeric antigen receptor of the present invention is not only capable of solving, through a reaction on/off switch, problems with cancer immunotherapy using existing CAR-T therapeutic agents such as persistent toxicity, risk of autoimmune disease, graft-versus-host disease (GVHD) for xenogeneic cell transplantation, and non-target toxicity, but is advantageous in that it allows various cancer cells to be targeted, and thus can be utilized as a general-purpose therapeutic agent. Since the CAR-NK cell of the present invention is capable of allogeneic transplantation, highly efficient cells can be premade as compared with CAR-T that uses the patient's own immune cells. Thus, the CAR-NK cell not only shortens timing of administration of a therapeutic agent to increase therapeutic efficacy thereof, but also can be usefully used for development of therapeutic agents for various diseases due to reduction of development and treatment costs.

As used herein, "antibody" refers to a substance produced by stimulation with an antigen in the immune system, and the type thereof is not particularly limited. In addition, in the present specification, the antibody includes, but is not limited to, fragments of the antibody which retain an antigen-binding ability, such as Fab, Fab', F(ab')2, and Fv.

As used herein, "chimeric antibody" refers to an antibody of which variable regions or complementarity determining regions (CDRs) thereof are derived from an animal that is different from the rest of the antibody. Such an antibody may be, for example, an antibody of which variable regions are derived from an animal (for example, a mouse, a rabbit, and poultry) other than a human and of which constant regions are derived from a human. Such a chimeric antibody may be produced by methods, such as genetic recombination, known in the art.

As used herein, "heavy chain" refers to both a full-length heavy chain and a fragment thereof, in which the full-length heavy chain includes a variable region domain VH having an amino acid sequence of a variable region which is sufficient to confer specificity to an antigen, and three constant region domains, CH1, CH2, and CH3.

As used herein, "light chain" refers to both a full-length light chain and a fragment thereof, in which the full-length light chain includes a variable region domain VL having an amino acid sequence of a variable region which is sufficient to confer specificity to an antigen, and a constant region domain CL.

The antigen binding domain constituting the chimeric antigen receptor of the present invention refers to a site where a main signal is transduced, the site being located outside the cell membrane and recognizing a cell membrane ligand (a substance that binds to and activates a receptor) of a target cell having a specific antigen.

The transmembrane domain of the present invention is a site that connects, across the cell membrane, the antigen binding domain with a co-stimulatory domain and an essential signaling domain. The intracellular signaling domain is a site that activates an immune response of an NK cell by binding of the antigen binding domain.

The chimeric antigen receptor of the present invention is characterized in that the antigen binding domain specifically binds to cotinine, and the cotinine refers to a major metabolic product of nicotine, which has a structure represented by the following Formula 1.

[Formula 1]

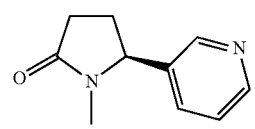

The cotinine is preferably a conjugate conjugated with a binding substance, and the binding substance may be characterized by being selected from the group consisting of peptides, aptamers, hormones, proteins, and chemical substances. The binding substance may be more preferably, but is not limited to, an aptamer.

In the present invention, the conjugate to which cotinine is conjugated may be produced by covalently attaching at least one polypeptide, typically one polypeptide, to at least one non-polypeptide moiety, as a heterologous molecule, such as a polymer molecule, a lipophilic compound, a carbohydrate moiety, or an organic derivatizing agent, in particular, a polymer moiety. In addition, the conjugate can be attached to at least one carbohydrate moiety, in particular, using N- or O-glycosylation. Covalent attachment means that the polypeptide and non-polypeptide moieties are directly covalently linked to each other, or indirectly covalently linked to each other via an intermediate moiety or portion, or the like, such as a linking bridge, a spacer, a linking moiety, or a moiety. For example, a conjugate obtained by conjugating the binding substance disclosed herein to cotinine is included in this definition.

In a complex in which an anti-cotinine antibody is bound to the conjugate of the binding substance with cotinine according to the present invention, the cotinine is used as a hapten so that the complex can retain both intrinsic properties of the binding substance and the antibody. Specifically, the complex may retain specific reactivities and functions of the molecules, and complement-mediated cytotoxicity (CDC), antibody-dependent cytotoxicity (ADCC), and a long in vivo half-life, which are characteristic of the antibody.

The binding substance may be, for example, selected from the group consisting of, for example, peptides, aptamers, hormones, proteins, and chemical substances, and may be, for example, selected from the group consisting of WKYMVm-NH2 peptide (WKYMVm-NH2), wkymvm-NH2 peptide (wkymvm-NH2), AS1411 aptamer, pegaptanib, abciximab, and insulin. In some embodiments of the invention, the protein may be an antibody, and may be specifically an anti-Her2 antibody or an anti-EGFR antibody.

Accordingly, the present invention provides a method for increasing an in vivo half-life of a binding substance by binding an anti-cotinine antibody to a conjugate obtained by conjugating the binding substance to cotinine.

In addition, the present invention provides a method for inducing complement dependent toxicity to a cell to which a binding substance binds by binding an anti-cotinine antibody to a conjugate obtained by conjugating the binding substance to cotinine.

The antigen binding domain of the present invention is a substance that specifically binds to cotinine, and may be an antibody or antibody fragment, wherein the antibody fragment may be scFv. Among sequences of the antibody or antibody fragment that binds to cotinine, cotinine-scFv may consist of, for example, the amino acid sequence represented by SEQ ID NO: 11, and may include, without limitation, sequences obtained as a result of modification or substitution thereof which have sequence homology, to the above amino acid sequence, of preferably 80% or more, more preferably 90% or more, and even more preferably 95% or more, and which exhibit substantially the same physiological activity as the amino acid sequence represented by SEQ ID NO: 11.

In addition, the cotinine-scFv may be encoded by the nucleotide sequence represented by SEQ ID NO: 17 and a nucleotide sequence which has sequence homology, to this nucleotide sequence, of preferably 80% or more, more preferably 90% or more, and even more preferably 95% or more.

In the anti-cotinine chimeric antigen receptor capable of specifically binding to cotinine, the antigen binding domain may consist of a heavy chain variable region, a linker sequence, and a light chain variable region. The light chain variable region may consist of an amino acid sequence encoded by the nucleotide sequence represented by SEQ ID NO: 1, or an amino acid sequence encoded by a nucleotide sequence which has sequence homology, to the nucleotide sequence represented by SEQ ID NO: 1, of 70% or more, preferably 80% or more, more preferably 90% or more, and even more preferably 95% or more, and which can encode a functional equivalent to an amino acid sequence expressed by the nucleotide sequence of SEQ ID NO: 1.

The heavy chain variable region may consist of an amino acid sequence encoded by the nucleotide sequence represented by SEQ ID NO: 2, or an amino acid sequence encoded by a nucleotide sequence which has sequence homology, to the nucleotide sequence represented by SEQ ID NO: 2, of 70% or more, preferably 80% or more, more preferably 90% or more, and even more preferably 95% or more, and which can encode a functional equivalent to an amino acid sequence expressed by the nucleotide sequence of SEQ ID NO: 2.

Amino acid sequences encoded by base sequences having 95% or more sequence homology, respectively, to the base sequence of SEQ ID NO: 1 or the nucleotide sequence of SEQ ID NO: 2 may exhibit substantially the same physiological activity as amino acid sequences encoded by the nucleotide sequences of SEQ ID NO: 1 and SEQ ID NO: 2.

The antibody or antibody fragment of the present invention may further include a linker, and the heavy chain variable region and the light chain variable region thereof may be linked to each other via the linker. The linker may be used without limitation as long as it is a component capable of linking the heavy chain variable region and the light chain variable region to form a VH-linker-VL domain. Preferably, the linker may consist of an amino acid sequence encoded by the nucleotide sequence of SEQ ID NO: 3 or a base sequence having 95% or more homology thereto.

The antigen binding domain in the anti-cotinine chimeric antigen receptor of the present invention may be linked to the transmembrane domain by a hinge region, a spacer region, or a combination thereof. The hinge region or spacer region of the present invention may be at least one selected from Myc epitope, CD8 hinge region, and Fc, and may preferably include Myc epitope and CD8 hinge region. The Myc epitope and the CD8 hinge region of the present invention function as a linking domain (spacer).

The CD8 hinge region of the present invention may consist of the amino acid sequence of SEQ ID NO: 12 or an amino acid sequence which has sequence homology, to SEQ ID NO: 12, of 70% or more, preferably 80% or more, more preferably 90% or more, and even more preferably 95% or more, and which exhibits a function substantially equivalent to the amino acid sequence represented by SEQ ID NO: 12; and the Myc epitope may consist of the amino acid sequence of SEQ ID NO: 13 or an amino acid sequence which has sequence homology, to SEQ ID NO: 13, of 70% or more, preferably 80% or more, more preferably 90% or more, and even more preferably 95% or more, and which exhibits a function substantially equivalent to the amino acid sequence represented by SEQ ID NO: 13. Thus, the hinge region or spacer region of the present invention preferably consists of the amino acid sequence of SEQ ID NO: 12 or an amino acid sequence having 95% or more homology thereto; or the amino acid sequence of SEQ ID NO: 13 or an amino acid sequence having 95% or more homology thereto.

In the present invention, the base sequence encoding the Myc epitope may include all nucleotide sequences capable of encoding the amino acid sequence of SEQ ID NO: 13 and may be preferably the nucleotide sequence of SEQ ID NO: 7; and the nucleotide sequence encoding the human CD8 hinge region may include all nucleotide sequences capable of encoding the amino acid sequence of SEQ ID NO: 12 and may be preferably the nucleotide sequence of SEQ ID NO: 4.

The transmembrane domain, which is a component of the chimeric antigen receptor of the present invention, may include a transmembrane domain of a protein selected from the group consisting of CD28, CD3 epsilon, CD45, CD4, CD5, CD8, CD9, CD16, CD22, CD33, CD37, CD64, CD80, CD86, CD134, CD137, and CD154. As an example, the transmembrane domain may be the transmembrane domain of CD28, which may consist of, but is not limited to, the amino acid sequence of SEQ ID NO: 16 or an amino acid sequence having 95% or more homology thereto.

In addition, for the intracellular signaling domain, which is a component of the chimeric antigen receptor of the present invention, intracellular signaling domains known in the art may be used without limitation. In an embodiment of the present invention, the intracellular signaling domain may include, but is not limited to, DAP10, CD3 zeta, or a combination thereof.

The chimeric antigen receptor of the present invention may use DAP10 and CD3 zeta as the intracellular signaling domain so that an NK cell can exhibit a killing effect on cancer cells with high activity. In this case, DAP10 functions as a co-stimulatory domain and may consist of the amino acid sequence of SEQ ID NO: 14 or an amino acid sequence which has sequence homology, to SEQ ID NO: 14, of 70% or more, preferably 80% or more, more preferably 90% or more, and even more preferably 95% or more, and which exhibits a function substantially equivalent to the amino acid sequence represented by SEQ ID NO: 14; and CD3 zeta functions as an NK cell activation domain and may consist of the amino acid sequence of SEQ ID NO: 15 or an amino acid sequence which has sequence homology, to SEQ ID NO: 15, of 70% or more, preferably 80% or more, more preferably 90% or more, and even more preferably 95% or more, and which exhibits a function substantially equivalent to the amino acid sequence represented by SEQ ID NO: 15. Thus, the intracellular signaling domain of the present invention may consist of the amino acid sequence of SEQ ID NO: 14 or an amino acid sequence having 95% or more homology thereto; or the amino acid sequence of SEQ ID NO: 15 or an amino acid sequence having 95% or more homology thereto.

In addition, the antigen binding domain of the present invention may include a signal peptide for exposure of domains. The signal peptide may be CD8 alpha or a mouse light chain kappa signal peptide. In a case of being CD8 alpha, the signal peptide of the present invention may consist of the amino acid sequence of SEQ ID NO: 10 or an amino acid sequence having 95% or more homology thereto. In addition, the base sequence encoding the CD8 alpha region may include all base sequences capable of encoding the amino acid sequence of SEQ ID NO: 10 and may be preferably the nucleotide sequence of SEQ ID NO: 6.

In addition, in the present invention, a vector which contains a polynucleotide capable of coding for (encoding) the above-described anti-cotinine chimeric antigen receptor may be used to transform an NK cell with the chimeric antigen receptor.

For the vector used in the present invention, various vectors known in the art may be used, in which an expression regulatory sequence such as a promoter, a terminator, and an enhancer, a sequence for membrane targeting or secretion, and the like may be appropriately selected, depending on the type of host cell in which the antigen receptor is intended to be produced, and may be combined in various ways depending on purposes. The vector of the present invention includes, but is not limited to, a plasmid vector, a cosmid vector, a bacteriophage vector, a viral vector, and the like. Suitable vectors include a signal sequence or a leader sequence for membrane targeting or secretion as well as expression regulatory elements such as promoter, operator, initiation codon, termination codon, polyadenylation signal, and enhancer, and may be constructed in various ways depending on purposes.

In the present invention, as a preferred example, a lentiviral vector (Clontech, 632155) may be used. Specifically, pLVX-AcGFP-C1, which is a vector used in the examples of the present invention, is illustrated in FIG. 1.

In some embodiments, the natural killer cell is obtained or produced from bone marrow, peripheral blood, peripheral blood mononuclear cells, or cord blood. In some embodiments, the cell is a human cell.

A schematic diagram of the NK cell expressing the anti-cotinine chimeric antigen receptor according to the present invention and an appearance of the cotinine conjugate are illustrated in FIG. 2.

The above-described NK cell which has been transformed by introduction of an antigen receptor can recognize cotinine as an antigen and specifically bind to the cotinine, and can express a cotinine-specific chimeric antigen receptor on the cell surface. Specifically, the receptor can induce the same activity as a CAR-NK cell, for example, to induce activation of the NK cell through an intracellular signaling domain upon contact and ligation with a tumor antigen, and induce tumor-specific killing of the NK cell.

Action of the Cot-CAR-NK cell, which is a cotinine-specific NK cell, according to the present invention is illustrated as a schematic view in FIG. 3.

In the present invention, in particular, the CAR-NK cell refers to a natural killer (NK) cell into which a chimeric antigen receptor has been introduced. The above-mentioned cell has the advantage of cancer-specific targeted therapy, which is an existing advantage of a CAR-T therapeutic agent, while having the following advantages: This cell not only can solve the toxicity problem, which is an existing problem, through a switch function capable of turning on/off a therapeutic response due to inclusion of the chimeric antigen receptor according to the present invention, but also can be used as a general-purpose therapeutic agent through terminal modification of a conjugate fused with cotinine that can be bound to the chimeric antigen receptor. That is, the NK cell expressing the chimeric antigen receptor that specifically binds to cotinine according to the present invention can effectively move to tumor tissue, regardless of the type of cancer, depending on a binding substance conjugated to cotinine. Accordingly, the cell according to the present invention can be usefully used as a gene therapeutic method that exhibits an excellent anti-cancer effect with high specificity.

Accordingly, in another aspect of the present invention, there is provided a cell therapeutic agent, comprising the natural killer cell, a pharmaceutical composition for the prevention or treatment of cancer, comprising the same as an active ingredient, or a method for preventing or treating cancer, comprising a step of administering the cell to an individual.

In the present invention, the cell may be used for cell therapy such as in anti-cancer treatment. The cell may be originated from a donor, or may be a cell obtained from a patient. The cell may be used, for example, for regeneration to replace the function of diseased cells. The cell may also be modified to express a heterologous gene so that a biological preparation can be delivered, for example, to a specific microenvironment such as diseased bone marrow or a metastatic deposit.

In addition, the pharmaceutical composition for the prevention or treatment of cancer of the present invention may further comprise a conjugate in which a binding substance is fused to cotinine, and the method for preventing or treating cancer may further comprise a step of administering a conjugate in which a binding substance is fused to cotinine. The natural killer cell can specifically bind to a target cell depending on the binding substance conjugated to cotinine, and exhibit an excellent anti-cancer effect.

Specifically, the cell provided in the present invention is a natural killer cell expressing a chimeric antigen receptor that has an antigen binding domain capable of specifically binding to cotinine, wherein the chimeric antigen receptor can, for example, regulate, with a conjugate fused to cotinine or an intermediate, on/off response of a conventional CAR therapeutic agent to a target cell. Thus, the natural killer cell includes a safety switch that can be very beneficial in situations where activity of a subsequent cell therapy or the therapeutic cell needs to be increased or decreased. For example, in a case where the NK cell expressing a chimeric antigen receptor is provided to a patient, in some circumstances, there may be side effects such as off-target toxicity. Alternatively, for example, the therapeutic cell may function to decrease the number of tumor cells or the tumor size, and may no longer be needed. In this situation, cotinine may be regulated, through which the therapeutic cell can be regulated to no longer be activated.

In the present invention, cancer may include, without limitation, all types of carcinomas known in the art.

As used herein, the term "unit dose" refers to a physically discrete unit suitable as a unitary dosage for a mammal, each unit containing a predetermined amount of pharmaceutical composition calculated to obtain a desired immunogen stimulating effect, together with a desired diluent. Details for the unit dose of inoculum are influenced by inherent characteristics of a pharmaceutical composition and specific immunological effects to be achieved, and determined accordingly.

An effective amount for a specific application may vary depending on factors such as the disease or condition to be treated, the specific composition to be administered, the size of a subject, and/or severity of the disease or condition. Without undue experimentation, the effective amount of a particular composition set forth herein may be determined in an empirical manner.

In addition, in yet another aspect of the present invention, there are provided a diagnostic composition for cancer and a diagnostic kit for cancer, each comprising a natural killer cell in which the chimeric antigen receptor (CAR) according to the present invention is expressed. In still yet another aspect of the present invention, there is provided a method for providing information for the diagnosis of cancer, comprising a step of bringing a composition containing a natural killer cell, in which the chimeric antigen receptor (CAR) of the present invention is expressed, into contact with a sample isolated from an individual. The composition or kit may further comprise, but is not limited to, a conjugate in which a binding substance is fused to cotinine.

As used herein, the term "diagnosis" is intended to include determining susceptibility of an subject to a particular disease or disorder, determining whether an individual currently has a particular disease or disorder, determining prognosis of an individual suffering from a particular disease or disorder, or therametrics (for example, monitoring status of an individual to provide information about therapeutic efficacy).

In still yet another aspect of the present invention, there is provided a use of a natural killer cell expressing the chimeric antigen receptor (CAR) for the prevention or treatment of cancer.

The chimeric antigen receptor, the natural killer cell expressing the same, and a use thereof for the prevention or treatment of cancer are as described above.

MODE FOR THE INVENTION

Hereinafter, the present invention will be described in more detail by way of examples. However, these examples are given to illustrate the present invention, and the scope of the present invention is not limited thereto.

Example 1. Vector Backbone

For the vector used in the present invention, a lentiviral vector (Clontech, 632155) was used. Specifically, pLVX-AcGFP-C1 illustrated in FIG. 1 was used. The Kozak sequence (CTCGAG; n.t. 2801-2806) and AcGFP1 (*Aequorea coerulescens* green fluorescent protein; n.t. 2807-3604) were deleted therefrom for use in the experiment, and then XhoI and XbaI were used as a restriction enzyme. A specific related sequence is illustrated in FIG. 4.

Example 2. Preparation of Target Antigen and Cotinine Conjugate

The chemical structure of cotinine (trans-4-cotininecarboxylic acid), which is a small molecule substance to be used as a target antigen, is shown in the following Formula 1. Cotinine purchased from Sigma-Aldrich was used.

[Formula 1]

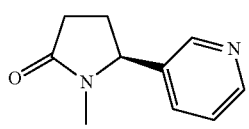

In addition, a conjugate in which cotinine and a binding substance are fused was prepared by the following method.

Specifically, for an HER2-cotinine conjugate, a conjugate in which cotinine and an anti-HER2 antibody are conjugated was prepared using Trastuzumab (Genentech, USA) which is the anti-HER2 antibody. Here, the conjugate was conjugated by the 1-ethyl-3-[3-dimethylaminopropyl]carbodiimide (EDC) coupling method. First, the anti-HER2 antibody was prepared by being dissolved in PBS to a concentration of 25 μM. On the other hand, trans-4-cotininecarboxylic acid (Sigma-Aldrich) was prepared by being dissolved in 1 ml of MES buffer [0.1 M 2-[morpholino]ethane sulfonic acid (MES) and 0.5 M sodium chloride, pH 6.0] to a concentration of 5 mM. To the resulting mixture were added EDC at a concentration of 50 mM and N-hydroxysulfosuccinimide (Sulfo-NHS, Thermo Scientific, USA) at a concentration of 125 mM. Then, the resultant was dissolved with stirring at room temperature for 15 minutes, to prepare an active solution in which cotinine-NHS ester was produced. In order to induce a reaction between the cotinine-NHS ester and an amine group of a protein, a sodium hydroxide solution was added to adjust the pH of the active solution to 7 or higher. 1 ml was taken therefrom. To this was added the anti-HER2 antibody to be conjugated to cotinine, at a concentration of 25 μM, in the same amount as the active solution. The mixture was allowed to react with stirring at room temperature for 3 hours, to obtain a cotinine-HER2 antibody conjugate produced through EDC coupling reaction. The obtained cotinine-HER2 antibody conjugate was dialyzed against PBS using the Slide-A-Lyzer™ Dialysis cassettes (Thermo Fisher Scientific, USA), or was subjected to replacement of the buffer with PBS using the Amicon Ultra Centrifugal Filter (EMD Millipore, USA) and used.

In addition, an EGFR-cotinine conjugate, as a conjugate in which an anti-EGFR affibody is fused with cotinine, purchased from ANYGEN (cotinine-zEGFR:95), was used. The specific sequence of the anti-EGFR affibody used is as follows.

trsn-4-cotininecarboxylic acid-VDNKFNKEM-WAAWEEIRNLPNLNGWQMTAFIASLVDDPSQSANL-LAEAKKL NDAQAPK (SEQ ID NO: 30)

Example 3. Anti-Cotinine Chimeric Antigen Receptor

A plasmid containing a nucleic acid which codes for each of the domains of a chimeric antigen receptor that specifically binds to cotinine of the present invention was prepared by the following method.

(1) Signal Peptide

Based on the human T-cell surface glycoprotein CD8 alpha chain (GenBank: AK300089.1), polymerase chain reaction was performed using two types of primers (forward primer: SEQ ID NO: 18, reverse primer: SEQ ID NO: 19) respectively containing restriction enzyme sites of XhoI and SfiI, and then cloning was performed.

(2) Target Specific Recognition Domain—scFv

As an antigen binding domain capable of specifically binding to cotinine, an anti-cotinine chimeric antibody or an antibody fragment thereof was intended to be obtained. For the sequence of ScFv, reference was made to information related to ScFv in Korean Patent No. 10-1648960. Specifically, the antigen binding domain includes the nucleotide sequence represented by SEQ ID NO: 17 and was constructed as VH-linker-VL.

(3) Linking Domain (Spacer)
(A) Myc Epitope

Based on the plasmid (anti-cotinine 28Z-1 CAR ORF, cot28z-1) possessed by the present inventors, polymerase chain reaction was performed using two types of primers (forward primer: SEQ ID NO: 20, reverse primer: SEQ ID NO: 21) respectively containing restriction enzyme sites of sfiI and HindIII, and then cloning was performed.

(B) Human CD8 Hinge Region

Based on the plasmid (anti-cotinine 28Z-1 CAR ORF, cot28z-1) possessed by the present inventors, polymerase chain reaction was performed with using two types of primers (forward primer: SEQ ID NO: 22, reverse primer: SEQ ID NO: 23) respectively containing a single restriction enzyme site of HindIII, and then cloning was performed.

(4) Transmembrane Region

The cytoplasmic region from the hinge of human CD28 gene was used as a transmembrane region. Primers were constructed by adding the sequence of restriction enzyme HindIII to a forward primer (SEQ ID NO: 24) and adding the sequence of restriction enzyme EcoRI to a reverse primer (SEQ ID NO: 25). PCR was performed on cDNAs of Jurkat cells using the above primers, to obtain a DNA of the transmembrane region.

(5) One or More Intracellular Signaling Domains
(A) Co-Stimulatory Domain

DAP10 was used as a co-stimulatory domain, and primers were constructed by adding the sequence of restriction enzyme EcoRI to a forward primer (SEQ ID NO: 26) and adding the sequence of restriction enzyme NotI to a reverse primer (SEQ ID NO: 27).

PCR was performed on cDNAs of primary mature NK cells using the above primers, to construct the co-stimulatory domain.

(B) NK Cell Activation Domain

CD3 zeta was used as an NK cell activation domain. Specifically, PCR was performed on cDNAs of Jurkat cells using two types of primers (forward primer: SEQ ID NO: 28, reverse primer: SEQ ID NO: 29), to construct the activation domain.

The above respective domains were sequentially ligated to one another using respective restriction enzymes, and specific sequence information corresponding to the respective domains is shown in Table 1 below.

TABLE 1

| SEQ ID NO | Sequence information | Description |
|---|---|---|
| 1 | GAGCTCGATCTGACCCAGACTCCAGCCTCCGTGTCTGC AGCTGTGGGAGGCACAGTCACCATCAATTGCCAGTCCA GTCAGAGTCCTTATAGTAACGAGTGGTTATCCTGGTAT CAGCAGAAACCAGGGCAGGCTCCCAAAGTCCTAATTTC TAGGATATCCACTCTGGCATCTGGGGTCTCATCGCGGT TCAAAGGCAGTGGATCTGGGACACAGTTCACTCTCACC ATAAGCGACCTGGAGTGTGGCGACGCTGCCACTTATTT CTGTGCAGGCGGTTATAATTTTGGTTTGTTTCCTTTCG GCGGAGGGACCGAGCTGGAGATCCTA | Light chain variable region |
| 2 | AGATCTTCCCAGTCGGTGAAGGAGTCCGAGGGTCGCCT GGTCACGCCTGGAGGATCCCTGACACTCACCTGCACAG TCTCTGGAATCGACCTCAGTAGGGACTGGATGAACTGG GTCCGCCAGGCTCCAGGGGAGGGGCTGGAATGGATCGG AGCCATTGGTAGAAGTGGAGACACATACTACGCGACCT GGGCGAAAGGCCGATTCACCATCTCCAAAACCTCGTCG AGGACGGTGACTCTAACAGTCACCGATCTGCAGCGCTC AGACACGGCCACCTATTTCTGTGCCAGAATTCCTTATT TTGGTTGGAATAATGGTGACATCTGGGGCCCAGGCACC CTGGTCACCATCTCTTCA | Heavy chain variable region |

TABLE 1-continued

| SEQ ID NO | Sequence information | Description |
|---|---|---|
| 3 | TCCTCTGGTGGCGGTGGCTCGGGCGGTGGTGGGGGTGG TTCCTCT | Linker |
| 4 | GGGGTCACCGTCTCTTCAGCGCTGAGCAACTCCATCAT GTACTTCAGCCACTTCGTGCCGGTCTTCCTGCCAGCGA AGCCCACCACGACGCCAGCGCCGCGACCACCAACACCG GCGCCCACCATCGCGTCGCAGCCCCTGTCCCTGCGCCC AGAGGCATGCCGGCCAGCGGCGGGGGCGCAGTGCACA CGAGGGGGCTGGA | Human CD8 hinge region |
| 5 | GTGAAAGGGAAACACCTTTGTCCAAGTCCCCTATTTCC CGGACCTTCTAAGCCCTTTTGGGTGCTGGTGGTGGTTG GTGGAGTCCTGGCTTGCTATAGCTTGCTAGTAACAGTG GCCTTTATTATTTTCTGGGTGAGGAGTAAGAGGAGCAG GCTCCTGCACAGTGACTACATGAACATGACTCCCCGCC GCCCCGGGCCCACCCGCAAGCATTACCAGCCCTATGCC CCACCACGCGACTTCGCAGCCTAT | CD28 |
| 6 | ATGGCCTTACCAGTGACCGCCTTGCTCCTGCCGCTGGC CTTACTGCTCCACGCCGCCAGGCCGGC | Human CD8 alpha region |
| 7 | GAACAAAAACTCATCTCAGAAGAGGATCTG | Myc epitope |
| 8 | CTGTGCGCACGCCCACGCCGCAGCCCCGCCCAAGAAGA TGGCAAAGTCTACATCAACATGCCAGGCAGGGGC | DAP10 |
| 9 | AGAGTGAAGTTCAGCAGGAGCGCAGACGCCCCCGCGTA CCAGCAGGGCCAGAACCAGCTCTATAACGAGCTCAATC TAGGACGAAGAGAGGAGTACGATGTTTTGGACAAGAGA CGTGGCCGGGACCCTGAGATGGGGGGAAAGCCGAGAAG GAAGAACCCTCAGGAAGGCCTGTACAATGAACTGCAGA AAGATAAGATGGCGGAGGCCTACAGTGAGATTGGGATG AAAGGCGAGCGCCGGAGGGGCAAGGGGCACGATGGCCT TTACCAGGGTCTCAGTACAGCCACCAAGGACACCTACG ACGCCCTTCACATGCAGGCCCTGCCCCCTCGCTAA | CD3 zeta |

When the sequences in Table 1 are matched to the structures described above, the signal peptide is represented by SEQ ID NO: 6 corresponding to the human CD8 alpha region; and among the target specific recognition domain, the light chain variable region is represented by SEQ ID NO: 1, the linker is represented by SEQ ID NO: 3, and the heavy chain variable region is represented by SEQ ID NO: 2. The linking domain (spacer) is represented by the Myc epitope of SEQ ID NO: 7 or the human CD8 hinge region of SEQ ID NO: 4, and CD28 as the transmembrane region is represented by SEQ ID NO: 5. For one or more intracellular signaling domains, DAP-10 as the co-stimulatory domain is represented by SEQ ID NO: 8, and CD3 zeta as the NK cell activation domain is represented by SEQ ID NO: 9.

Example 4: Production of NK Cell into which Anti-Cotinine Chimeric Antigen Receptor has been Introduced The polynucleotide coding for the anti-cotinine chimeric antigen receptor presented in Example 3 was introduced into a vector, and the resulting vector was used to produce a transformed natural killer cell. Schematic diagrams for a chimeric antigen receptor containing a cotinine-specific antigen binding domain and an expression system thereof are illustrated in FIG. 5.

First, using, as a basic vector, the vector obtained by removing AcGFP from pLVX-AcGFP-C1 of Example 1, the polynucleotide coding for the anti-cotinine chimeric antigen receptor of Example 3 (cotinine-CAR) was inserted into the vector using restriction enzymes XhoI and XbaI of MCS therein.

Next, HEK293T cells were transformed by the vector containing the cotinine-CAR together with viral packaging vectors (PMDLg/RRE, RSV/REV, VSVG), and lentivirus expressing the cotinine-CAR was obtained therefrom. The lentivirus was concentrated using an ultra-high-speed centrifuge, and the concentrated lentivirus expressing the cotinine-CAR was used to infect HEK293T or Hela cells. Then, the amount of Myc epitope of the cotinine-CAR was identified with flow cytometry to calculate infection unit. The number of NK cells and the amount of lentivirus were calculated so that the multiplicity of infection (MOI) was 30, and the lentivirus expressing the cotinine-CAR was used to infect NK cells by the spinoculation method (360 g, 90 min, RT). The infected NK cells were cultured for 5 hours at a condition of 37° C. and 5% $CO_2$, and then the culture medium was replaced with a fresh culture medium. After 3 days, treatment with puromycin at a concentration of 3 ug/ml was performed for selection of infected NK cells, and the culture was continued.

Uninfected NK cells as a control were also treated with puromycin, wherein the culture was continued using a puromycin-treated culture medium until the control cells were completely killed by puromycin. At a time point when the control cells were completely killed, for the infected NK cells, the culture medium was exchanged for a puromycin-free medium for proliferation or expansion. For proliferation or expansion of the selected cells, experiments were carried out using a medium with alpha-MEM-containing 12.5% fetal bovine serum, 12.5% horse serum, 0.2 mM inositol, 0.1 mM 2-mercaptoethanol, 0.02 mM folic acid, and 200 U/ml recombinant IL-2.

Example 5. Identification of Expression of CAR in NK Cell into which Anti-Cotinine Chimeric Antigen Receptor has been Introduced Expression of CAR in the NK cells produced in Example 4 into which the anti-cotinine chimeric antigen receptor of the present invention had been introduced was identified with flow cytometry.

An Myc antibody (CTS; 9B11) corresponding to the Myc epitope of the cotinine-CAR was allowed to react with the NK cells expressing the cotinine-CAR (4° C., 30 minutes in the dark) and expression of Myc was identified with flow cytometry; or a cotinine conjugate with which an Her2 antibody is fused was allowed to react with the NK cells expressing the cotinine-CAR at 4° C. for 30 minutes, a secondary reaction was performed with an Fc antibody (eBioscience; 12-4988-82) corresponding to the Fc region of the Her2 antibody, and then identification was made with flow cytometry. As a control, original NK92 cells not expressing CAR were used, and the results are illustrated in FIG. 6.

As illustrated in FIG. 6, it was confirmed that the NK cell of the present invention into which the anti-cotinine chimeric antigen receptor had been introduced expressed an anti-cotinine antibody fragment.

Example 6. Confirmation of Binding Specificity of Cotinine-CAR NK Cell to Cotinine Cot-SWNT, a cotinine polymer, and HER2-tumor cells were used to confirm whether cotinine ScFv of the cotinine-CAR NK cells specifically binds to cotinine.

Specifically, AU565 (human breast carcinoma) was stained with calcein-AM (Life Technologies; C1430). Then, the NK cells expressing the cotinine-CAR were mixed therewith at a ratio of 1:1 in 200 ul of RPMI1640 (10% FBS), and the mixture was subjected to simultaneous treatment with a cotinine conjugate fused with an Her2 antibody at a concentration of 1 ug/ml and cot-SWNT at concentrations (0, 0.005, 0.05, 0.5, and 5 mg/ml) so that competition occurred between the cot-SWNT and the Her2-cotinine conjugate (Her2-cot). In addition, in order to identify an effect of cot-SWNT alone, a condition for treatment with cot-SWNT (5 mg/ml) alone was added and treatment was performed under this condition. After the reaction was allowed to proceed at 37° C. and 5% $CO_2$ for 4 hours, 100 µl of the supernatant was taken and the amount of calcein present in the supernatant was identified, thereby identifying a cell killing effect depending on each condition. As controls, a group (spontaneous value) in which AU565 stained with calcein was treated with RPMI1640 (10% FBS) only and a group (maximum value) in which AU565 stained with calcein was treated with 2% Triton X-100 were used, and a cell killing effect was calculated by the following method.

Cell killing effect (%)=(calcein release value depending on condition−spontaneous value)/ (maximum value−spontaneous value)×100

The result for the cell killing effect thus obtained is illustrated in FIG. 7.

As illustrated in FIG. 7, it was found that as the concentration of cot-SWNT increased, a killing effect of the cotinine-CAR NK cells on cancer cells expressing her2 decreased. From this, it was confirmed that the cotinine-CAR NK cell of the present invention acted specifically on target cells depending on a binding substance of the conjugate.

Example 7. Confirmation of Cell Killing Effect of Cotinine-CAR NK Cell Through by Herceptin (Her2)-Cotinine Conjugate Using the anti-Her2-cotinine conjugate prepared in Example 3 and the cotinine-CAR NK92 cell produced in Example 4, it was found that the conjugate recognizes Her2 on the cancer cell surface so that a cell killing effect is exerted by the NK cell into which the anti-cotinine chimeric antigen receptor of the present invention has been introduced.

First, each of four cell lines, AU565 (human breast carcinoma; RPMI1640 (10% FBS; 200 nm HEPES)), SK-OV-3 (human ovarian carcinoma; RPMI1640 (10% FBS)), SK-BR-3 (human breast carcinoma; DMEM (10% FBS)), and K562 (chronic myelogenous leukemia; RPMI1640 (10% FBS)) was treated with an anti-Her2 antibody (Invitrogen; BMS120FI) in an amount of 1 ug/100 ul, and the reaction was allowed to proceed at 4° C. for 30 minutes in the dark. After the reaction, for each cell line, an expression level of Her2 therein was examined with flow cytometry (BD; FacsCantoII). The results are illustrated in FIG. 8.

As illustrated in FIG. 8, it was found that Her2 was expressed in AU565, SK-OV-3, and SK-BR-3 cells, but Her2 was not expressed in K562 cells.

Next, a cell killing effect of cotinine-CAR NK cells depending on the presence or absence of the Her2-cotinine conjugate was examined through the calcein-AM method. Specifically, each of the four cell lines, AU565, SK-OV-3, SK-BR-3, and K562 was treated with calcein-AM at a concentration of 5 ug/ml, and then the reaction was allowed to proceed for 1 hour at a condition of 37° C. and 5% $CO_2$ in the dark. After the reaction, original NK92, NK92 (Puro-92) into which a control vector expressing a pLVX empty vector with AcGFP deleted was inserted, and cotinine-CAR NK92 (cotinine-CAR-NK) were respectively mixed with the above cell lines at a ratio of 5:1, 1:1, and 0.5:1 (effector cell; NK92, Puro-92, Cotinine-CAR-NK:target cell; AU565, SK-OV-3, SK-BR-3, K562) in 200 ul of RPMI (10% FBS), and the reaction was allowed to proceed for 4 hours at a condition of 37° C. and 5% $CO_2$. Then, 100 µl of supernatant was taken and the amount of calcein present in the supernatant was examined, thereby identifying a killing effect depending on each condition. The results are illustrated in FIG. 9.

As illustrated in FIG. 9, it was found that the cotinine-CAR NK92 cell exhibited a cell killing activity for AU565, SK-OV-3, and SK-BR-3 cells which express Her2, while not exhibiting activity for K562 cells in which Her2 is not expressed. In addition, it was identified that the Her2-cotinine conjugate did not affect a cell killing effect of NK92 and Puro-92, but had an effect on cotinine-CAR NK92. From these results, it was confirmed that the cotinine-CAR NK cell of the present invention specifically induced cell killing through the cotinine-conjugate.

Example 8. Verification of Cellular Activity of Cotinine-CAR NK Cell

Activity of NK cells was verified by examining secretion of cytokines and granules in the NK cells. Specifically, secretion of cytokines was verified as follows. Each of original NK92, PURO-92, and cotinine-CAR-NK was mixed with AU565 at 1:1 in RPMI1640 (10% FBS). To this was added the cotinine conjugate, and the reaction was allowed to proceed for 6 hours at a condition of 37° C. and 5% $CO_2$. Then, the supernatant was collected and cytokines IFN-r and TNF-α which were present in the supernatant were verified through ELISA. The amount of cytokines secreted by each of the original NK92, PURO-NK92, and cotinine-CAR-NK alone was used as a control, and the results are illustrated in FIG. 10.

In addition, expression of CD107a was verified as follows. Each of original NK92, PURO-92, and cotinine-CAR-NK was mixed with AU565 at 1:1 in RPMI1640 (10% FBS). The mixture was treated with the cotinine conjugate and CA107a antibody (BD; 555801) in combination, and then the reaction was allowed to proceed for 4 hours at a condition of 37° C. and 5% $CO_2$. Staining was performed using CD56 antibody so that NK92 cells can be selected from the cells after the reaction. Then, expression levels of CD107a in the original NK92, PURO-NK92, and cotinine-CAR-NK were compared using flow cytometry. As controls, basic expression levels of CD107a in the original NK92, PURO-92, and Cotinine-CAR-NK, and expression levels of CD107a therein in a state of being mixed with AU565 in the absence of the cotinine conjugate were used, and the results are illustrated in FIG. 11.

As illustrated in FIGS. 10 and 11, it was found that secretion of cytokines and granules in NK cells occurred in response to cancer cells only in a case where the cotinine-CAR NK cell and the Her2-cotinine conjugate were present.

Example 9. Changes in Signal of Cotinine-CAR NK Cell Caused by Her2-Cotinine Conjugate Activity of the cotinine-CAR NK cells was examined by measuring the signal that changes when the NK cells exhibit activity. Specifically, phosphorylation of Erk was examined with flow cytometry using a signal that passes through the endodomain of the cotinine-CAR NK92, and the results are illustrated in FIG. 12.

As illustrated in FIG. 12, it was found that phosphorylation of intracellular Erk did not increase in a case where the cotinine-CAR NK92 cells were present alone (without her2-cot; control), and phosphorylation of Erk in the cotinine-CAR NK92 cells increased due to the her2-cotinine conjugate (her2-cot) in a case where cancer cells were present (with her2-cot; her2-cot-treated group).

Example 10. Verification of Specificity of Herceptin (Her2)-Cotinine Conjugate for Cotinine-CAR NK Cell In order to verify specificity of cotinine-CAR NK cells for the Her2-cotinine conjugate, a cell killing effect depending on the conjugate was examined.

First, a respiratory syncytial virus (RSV)-cotinine conjugate was used as a control for the Her2-cotinine conjugate. The RSV-cotinine conjugate was prepared in the same manner as in Example 2 except that an anti-RSV antibody (Palivizumab, Synagis®, AstraZeneca, UK) was used as an antibody to be fused with cotinine in the method for preparing a cotinine conjugate of Example 2.

Next, the cotinine-CAR-NK cells and calcein-stained AU565 were mixed at a ratio of 5:1, 1:1, and 0.5:1, respectively, in RPMI1640 (10% FBS) and treatment with the Her2-cotinine conjugate for Her2, which is an antigen expressed on AU565 cells, and the non-expressed respiratory syncytial virus antibody (RSV; Palivizumab; Synagis®, AstraZeneca, UK)-cotinine conjugate, each at a concentration of 1 ug/ml, was performed. The reaction was allowed to proceed for 4 hours at a condition of 37° C. and 5% $CO_2$. Then, a cell killing effect of the cotinine-CAR NK92 cells was examined through the calcine-AM method, and the result is illustrated in FIG. 13.

As illustrated in FIG. 13, it was found that the cotinine-CAR NK cells specifically exhibited activity to the Her2-cotinine conjugate.

Example 11. Verification of Cell Killing Effect of Cotinine-CAR NK Cell Caused by Herceptin (Her2)-Cotinine Conjugate and EGFR (Affibody)-Cotinine Conjugate Using the anti-Her2-cotinine conjugate prepared in Example 3 and the anti-EGFR-cotinine conjugate together with the cotinine-CAR NK92 cell produced in Example 4, it was verified that a cell killing effect is exerted by the NK cell into which the anti-cotinine chimeric antigen receptor of the present invention has been introduced through the recognition of Her2 or EGFR on the cancer cell surface by the cotinine conjugate.

First, each of four cell lines, AU565 (human breast carcinoma), SK-OV-3 (human ovarian carcinoma), A431 (human skin carcinoma; DMEM (10% FBS)), and A549 (human lung carcinoma; RPMI1640 (10% FBS)) was treated with an anti-Her2 antibody and an anti-EGFR antibody (BD; 563577), each in an amount of 1 ug/100 ul, and the reaction was allowed to proceed at 4° C. for 30 minutes in the dark. Then, for each cell line, expression levels of Her2 and EGFR therein were examined with flow cytometry, and the results are illustrated in FIG. 14.

As illustrated in FIG. 14, it was found that expression levels of Her2 and EGFR in the four cell lines are different depending on each cell line.

Next, for each of the four cell lines, a cell killing effect of the cotinine-CAR NK92 depending on the presence or absence of the Her2-cotinine conjugate or the EGFR-cotinine conjugate was examined through the calcine-AM method. Specifically, each of AU565, SK-OV-3, A431, and A549 cells was stained with calcein, and then was mixed with cotinine-CAR-NK cells at a ratio of 5:1, 1:1, and 0.5:1 (cotinine-CAR-NK:cancer cell) in 200 ul of RPMI1640 (10% FBS). Depending on each condition, only cotinine-CAR-NK and the cancer cells were allowed to react, or cotinine-CAR-NK and the cancer cells were allowed to react together with treatment with the Her2-cotinine conjugate (1 ug/ml) or EGFR-cotinine conjugate (100 ng/ml). The reaction was allowed to proceed for 4 hours at a condition of 37° C. and 5% $CO_2$. A cell killing effect depending on each condition was examined, and the results are illustrated in FIG. 15.

As illustrated in FIG. 15, the cotinine-CAR NK92 cell exhibited a cell killing effect depending on an expression level of the target antigen, Her2 or EGFR, which confirms that a cell killing effect of the cotinine-CAR NK cell of the present invention depended on the type of a cotinine conjugate.

Example 12. Verification of Cellular Activity of Cotinine-CAR NK Cell Caused by zEGFR-Cot Conjugate Changes in activity, against cancer cells expressing Her2 or EGFR, caused by the her2-cotinine conjugate or EGFR-cotinine conjugate were examined by secretion of cytokines and granules.

Specifically, AU565 or A431 cells and cotinine-CAR-NK were mixed at a ratio of 1:1 in RPMI1640 (10% FBS). Treatment with the her2-cot conjugate or zEGFR-cot conjugate was performed, and then the reaction was allowed to proceed for 6 hours at a condition of 37° C. and 5% $CO_2$. Then, changes in secretion of cytokines (IFN-r and TNF-a) in the supernatant were examined using ELISA, and the results are illustrated in FIG. 16.

In addition, secretion of granules was examined by an expression level of CD107a. Specifically, each of original NK92, PURO-92, and cotinine-CAR-NK was mixed with AU565 or A431 cells at 1:1. The mixture was treated with the her2-cot conjugate or zEGFR-cot conjugate, and treated with CD107a antibody. The reaction was allowed to proceed for 4 hours at a condition of 37° C. and 5% $CO_2$. Staining was performed using CD56 antibody so that NK92 cells can be selected after the reaction. Then, examination was made with flow cytometry. The results for the AU565 and A431 cells are illustrated in FIGS. 17 and 18, respectively.

As illustrated in FIGS. 16 to 18, it was found that activity of the cotinine-CAR NK cell increased due to the antibody-cotinine conjugate against an antigen.

Example 13. Verification of Cellular Activity of Cotinine-CAR NK Cell Caused by EGFR-Cotinine Conjugate in Lung Cancer Metastasis Model In order to verify cellular activity of the cotinine-CAR NK cell caused by the EGFR-cotinine conjugate in a lung cancer metastasis model, an experiment was conducted according to the schedule as illustrated in FIG. 19.

First, $2 \times 10^6$ A549-Luc cells were administered into the tail vein. After 6 hours, 2 days, 4 days, 7 days, and 9 days, treatment with $1 \times 10^7$ cotinine-CAR-NK (Cot-CAR-NK) cells was performed in the presence and absence of the EGFR-cotinine conjugate (zEGFR-COT). On the other hand, Taxol, which is an anti-cancer substance, was administered in an amount of 10 mg/kg as a positive control group at days 2, 4, 7, and 9 after inoculation with the A549-Luc cells. As such, in this experiment, the experiment was conducted using the groups which were divided into three groups (Taxol, α-COT-92, and α-COT-92 and zEGFR-COT), and each treatment substance was administered into the tail vein of 10 mice per each group (30 mice total).

In order to capture a bioluminescent image, D-luciferin (150 mg/kg body weight) was injected into the mouse abdominal cavity immediately before capture, anesthesia was performed with isoflurane, and then a bioluminescence image was measured with the in vivo imaging system (IVIS). Specifically, starting from 1 day after administration of the A549 lung cancer cells into the tail vein, the lung cancer development and metastasis pattern in each group according to the presence and absence of zEGFR-COT was checked once a week for 10 weeks, in which an anti-cancer effect of the α-COT-92 cells caused by the EGFR-cotinine conjugate was examined through the bioluminescence image. The results are illustrated in FIG. 20. In addition, the mean total flux for the bioluminescence measured in the three groups is graphically illustrated (FIG. 21).

At 70 days after administration of each treatment substance, the mice were sacrificed, the lungs were extracted therefrom, and nodules formed in the lungs were identified through bioluminescence images. The nodules appeared in various sizes and numbers. The results are illustrated in FIG. 22. As illustrated in FIG. 22, in the α-COT-92 cell-treated group, lung cancer developed because CAR did not recognize EGFR of cancer cells; and the Taxol-treated group and the α-EGFR-COT and α-COT-92 cell-treated group, which were used as positive controls, exhibited an anti-cancer effect at a significant level. In addition, while the experiment was conducted, there was no remarkable difference in the mean body weight values of mice in the three groups (FIG. 23).

Example 14. Verification of Cellular Activity of Cotinine-CAR NK Cell Caused by EGFR-Cotinine Conjugate in Lung Cancer Growth Inhibition Model In order to verify cellular activity of the cotinine-CAR NK cell caused by the EGFR-cotinine conjugate in a lung cancer growth inhibition model, an experiment was conducted according to the schedule as illustrated in FIG. 24.

First, $2 \times 10^6$ A549-Luc cells were administered into the tail vein. After 2 days, 4 days, 7 days, and 9 days, treatment with 100 μL of PBS (negative control), 10 mg/kg of Taxol (positive control), and $3 \times 10^6$ conventional α-EGFR-92 cells was performed, and treatment with $3 \times 10^6$ cotinine-CAR-NK cells was performed in the presence and absence of the EGFR-cotinine conjugate (zEGFR-COT). As such, in this experiment, the experiment was conducted using the groups which were divided into five groups (PBS (Non), Taxol, α-COT-92 (NK), α-COT-92 and zEGFR-COT (CAR-NK), and α-EGFR-92 (EGFR)), and each treatment substance was administered into the tail vein of 10 mice per each group (total of 50 mice total).

In order to capture a bioluminescent image, D-luciferin (150 mg/kg body weight) was injected into the mouse abdominal cavity immediately before capture, anesthesia was performed with isoflurane, and then a bioluminescence image was measured with the in vivo imaging system (IVIS). Specifically, at 50 days after administration of the A549 lung cancer cells into the tail vein, the lung cancer development and metastasis pattern in each group was checked, in which an anti-cancer effect of the α-COT-92 cells caused by the EGFR-cotinine conjugate was examined through the bioluminescence image. The results are illustrated in FIG. 25.

In addition, the mean total flux for the bioluminescence measured in the five groups is graphically illustrated (FIG. 26). Here, in FIG. 26, Non means PBS, NK means α-COT-92, CAR-NK means α-COT-92 and zEGFR-COT, and EGFR means α-EGFR-92. As illustrated in FIG. 26, mice in the PBS-treated group rapidly progressed to lung cancer; and the α-COT-92 cell-treated group, although it did not recognize a cancer-specific marker through CAR, showed a slight cancer cell inhibitory effect due to characteristics of NK cell. In addition, the Taxol-treated group, the α-EGFR-92 cell-treated group, and the α-COT-92 and α-EGFR-COT cell-treated group exhibited an anti-cancer effect at a significant level.

In the foregoing, specific parts of the present invention have been described in detail. It will be apparent to those skilled in the art that this specific description only shows preferred embodiments and that the scope of the present invention is not limited thereto. Accordingly, the actual scope of the present invention will be defined by the appended claims and equivalents thereof.

The invention claimed is:

1. A chimeric antigen receptor (CAR)-expressing natural killer cell, wherein the chimeric antigen receptor comprises
1) An antigen binding domain,
2) a transmembrane domain, and
3) an intracellular signaling domain,
wherein the 1) antigen binding domain is an antibody or antibody fragment thereof that specifically binds to cotinine,
wherein the 3) intracellular signaling domain is derived from DAP10 and CD3 zeta,
wherein the antibody or antibody fragment thereof comprises a heavy chain variable region consisting of the amino acid sequence encoded by the nucleotide sequence of SEQ ID NO: 2, and
a light chain variable region consisting of the amino acid sequence encoded by the nucleotide sequence of SEQ ID NO: 1.

2. The CAR-expressing natural killer cell of claim 1, wherein the antibody fragment is scFv.

3. The CAR-expressing natural killer cell of claim 1, wherein the antibody or antibody fragment further comprises a linker.

4. The CAR-expressing natural killer cell of claim 3, wherein the linker consists of the amino acid sequence encoded by the nucleotide sequence of SEQ ID NO: 3.

5. The CAR-expressing natural killer cell of claim 1, wherein the 1) antigen binding domain is linked to the 2) transmembrane domain by a hinge region, a spacer region, or a combination thereof.

6. The CAR-expressing natural killer cell of claim 5, wherein the hinge region, the spacer region, or the combination thereof is at least one selected from Myc epitope, CD8 hinge region, and Fc.

7. The CAR-expressing natural killer cell of claim 1, wherein the 2) transmembrane domain comprises a transmembrane domain of at least one protein selected from the group consisting of CD28, CD3 epsilon, CD45, CD4, CD5, CD8, CD9, CD16, CD22, CD33, CD37, CD64, CD80, CD86, CD134, CD137, and CD154.

8. The CAR-expressing natural killer cell of claim 7, wherein the 2) transmembrane domain comprises the transmembrane domain of CD28.

9. The CAR-expressing natural killer cell of claim 1, wherein the 1) antigen binding domain comprises a signal peptide.

10. The CAR-expressing natural killer cell of claim 9, wherein the signal peptide is CD8a or a mouse light chain kappa signal peptide.

11. The CAR-expressing natural killer cell of claim 1, wherein the cotinine is in the form of a complex conjugated with a binding substance.

12. The CAR-expressing natural killer cell of claim 11, wherein the binding substance is selected from the group consisting of a peptide, aptamer, hormone, protein, and a chemical compound.

13. A pharmaceutical composition, comprising as an active ingredient the CAR-expressing natural killer cell of claim 1.

14. A method for treating cancer in a subject in need thereof, comprising administering an effective amount of the CAR-expressing natural killer cell of claim 1 to the subject.

15. The method of claim 14, wherein the CAR-expressing natural killer cell is an autologous NK cell or an allogeneic NK cell.

* * * * *